United States Patent
Sheppard et al.

(10) Patent No.: US 11,008,539 B2
(45) Date of Patent: May 18, 2021

(54) METHODS FOR THE PRODUCTION OF FERMENTED BEVERAGES AND OTHER FERMENTATION PRODUCTS

(71) Applicant: NORTH CAROLINA STATE UNIVERSITY, Raleigh, NC (US)

(72) Inventors: John Sheppard, Raleigh, NC (US); Robert Dunn, Raleigh, NC (US); Anne Madden, Boulder, CO (US)

(73) Assignee: North Carolina State University, Raleigh, NC (US)

( * ) Notice: Subject to any disclaimer, the term of this patent is extended or adjusted under 35 U.S.C. 154(b) by 426 days.

(21) Appl. No.: 15/573,652

(22) PCT Filed: May 13, 2016

(86) PCT No.: PCT/US2016/032403
§ 371 (c)(1),
(2) Date: Nov. 13, 2017

(87) PCT Pub. No.: WO2016/187021
PCT Pub. Date: Nov. 24, 2016

(65) Prior Publication Data
US 2018/0119074 A1    May 3, 2018

Related U.S. Application Data

(60) Provisional application No. 62/162,379, filed on May 15, 2015.

(51) Int. Cl.
| | | |
|---|---|---|
| C12C 12/00 | (2006.01) | |
| C12C 11/00 | (2006.01) | |
| C12P 7/06 | (2006.01) | |
| C12R 1/645 | (2006.01) | |
| C12P 7/56 | (2006.01) | |
| C12G 3/022 | (2019.01) | |
| C12G 3/023 | (2019.01) | |
| C12G 3/024 | (2019.01) | |

(52) U.S. Cl.
CPC .......... *C12C 12/006* (2013.01); *C12C 11/003* (2013.01); *C12G 3/022* (2019.02); *C12G 3/023* (2019.02); *C12G 3/024* (2019.02); *C12P 7/06* (2013.01); *C12P 7/56* (2013.01); *C12R 1/645* (2013.01); *Y02E 50/10* (2013.01)

(58) Field of Classification Search
CPC ..... A23L 2/02; A23L 2/38; A23L 2/84; A23L 2/52; C12N 1/04; C12N 1/16; C12N 1/18; C12G 1/0203; C12G 3/02; C12C 12/006; C12C 11/003; C12R 1/645
USPC ......................................... 426/16, 590, 592
See application file for complete search history.

(56) References Cited

U.S. PATENT DOCUMENTS

2006/0257529 A1* 11/2006 Sommer .............. C12G 1/0203
426/62

FOREIGN PATENT DOCUMENTS

| WO | 2004/072271 A1 † | 8/2004 | |
| WO | WO-2011134952 A1 * | 11/2011 | ............... A23L 2/02 |
| WO | WO 2013/068999 | 5/2013 | |

OTHER PUBLICATIONS

Gobbi M. et al., "Lachancea thermotolerans and *Saccharomyces cerevisiae* in simultaneous and sequential co-fermentation: a strategy to enhance acidity and improve the overall quality of wine", Food Microbiology, vol. 33, pp. 271-281 (2013).
Written Opinion and International Search Report corresponding to International Application No. PCT/US2016/032403, dated Aug. 18, 2016, 12 pages.
Brickwedde et al. "Structural, Physiological and Regulatory Analysis of Maltose Transporter Genes in *Saccharomyces eubayanus* CBS 12357T" Frontiers in Microbiology, vol. 9, article 1786, 2018.
Carlson "Regulation of Sugar Utilization in *Saccharomyces* Species" J. Bacteriol., 169(11):4873-4877 1987.
Domizio et al. "Lachancea thermotolerans as an alternativeyeast for the production of beer" J Institute of Brewing, 122(4):599-604 2016.
Jansen et al. "Prolonged Maltose-Limited Cultivation of *Saccharomyces cerevisiae* Selects for Cells with Improved Maltose Affinity and Hypersensitivity" Appl Environ Microbiol., 70(4):1956-1963 2004.
Kelebek et al. "HPLC determination of organic acids, sugars, phenolic compositions and antioxidant capacity of orange juice and orange wine made from a Turkish cv. Kozan" Microchemical Journal, 91(2):187-192 2009.
Lopez-Malo et al. "Metabolomic Comparison of *Saccharomyces cerevisiae* and the Cryotolerant Species *S. bayanus* var. uvarum and *S. kudriavzevii* during Wine Fermentation at Low Temperature" Plos One, 8(3):e60135 2013.
Ostergaard et al. "Metabolic Engineering of *Saccharomyces cerevisiae*" Micro. Mol. Biol. Rev. 64(1):34-50 2000.
Walker et al. "*Saccharomyces cerevisiae* in the Production of Fermented Beverages" Beverages. 2(30): 12p, 2016.
UniProt entry entitled "Proteomes—Lachancea thermotolerans (strain ATCC 56472 / CBS 6340 / NRRL Y-8284) (Yeast) (Kluyveromyces thermotolerans)" (https://www.uniprot.org/proteomes/UP000002036;); last modified on Aug. 19, 2020.
Skerman, et al., Approved Lists of Bacterial Names (Amended) ASM Press (found at https://www.ncbi.nlm.nih.gov/books/NBK816/) (see paragraph bridging pp. 3-4)) (1989).
Yarrow D., "Four new combinations in Yeast", Antonie van Leeuwenhoek, 38:357-360 1972.
Marc-Andre Lachance, Current status of Kluyveromyces systematics, 642-645,2007, Blackwell Publishing Ltd., FEMS Yeast Res 7.†

\* cited by examiner
† cited by third party

*Primary Examiner* — Vera Stulii
(74) *Attorney, Agent, or Firm* — Myers Bigel, P.A.

(57) ABSTRACT

The present invention is directed to methods for making fermented beverages and other fermentation products including lactic acid and ethanol for fuel and the products produced therefrom.

7 Claims, 13 Drawing Sheets

Fig. 2

| | YB16 | BB202 | Lachancea thermotolerans | Lachancea meyersii | Kluyveromyces (Lachancea) waltii | Lachancea dasiensis | Lachancea lanzarotensis | Lachancea fermentati | Zygosaccharomyces (Lachancea) cidri | Saccharomyces (Lachancea) kluyveri |
|---|---|---|---|---|---|---|---|---|---|---|
| YB16 | 100 | 98 | 99 | 95 | 97 | 96 | 93 | 91 | 91 | 88 |
| BB202 | -- | 100 | 99 | 94 | 96 | 95 | 93 | 90 | 90 | 87 |
| Lachancea thermotolerans | -- | -- | 100 | 94 | 96 | 96 | 93 | 91 | 90 | 90 |
| Lachancea meyersii | -- | -- | -- | 100 | 94 | 96 | 97 | 90 | 90 | 88 |
| Kluyveromyces (Lachancea) waltii | -- | -- | -- | -- | 100 | 96 | 94 | 92 | 91 | 89 |
| Lachancea dasiensis | -- | -- | -- | -- | -- | 100 | 96 | 93 | 93 | 88 |
| Lachancea lanzarotensis | -- | -- | -- | -- | -- | -- | 100 | 90 | 91 | 89 |
| Lachancea fermentati | -- | -- | -- | -- | -- | -- | -- | 100 | 98 | 90 |
| Zygosaccharomyces (Lachancea) cidri | -- | -- | -- | -- | -- | -- | -- | -- | 100 | 89 |
| Saccharomyces (Lachancea) kluyveri | -- | -- | -- | -- | -- | -- | -- | -- | -- | 100 |

METHODS FOR THE PRODUCTION OF FERMENTED BEVERAGES AND OTHER FERMENTATION PRODUCTS

STATEMENT OF PRIORITY

This application is a 35 U.S.C. § 371 national phase application of International Application Serial No. PCT/US2016/032403, filed May 13, 2016, which claims the benefit, under 35 § 119 (a) of U.S. Provisional Patent Application No. 62/162,379, filed May 15, 2015, the entire contents of each of which are incorporated by reference herein.

FIELD OF THE INVENTION

The invention relates to methods for making fermented beverages and other fermentation products such as lactic acid and ethanol for fuel, and the products produced therefrom.

BACKGROUND OF THE INVENTION

Yeast are important industrial microorganisms that have played a primary role in the production of numerous foods and beverages for centuries. *Saccharomyces* spp. have the ability to ferment carbohydrates originating from starchy plant materials into more palatable, nutritious and shelf-stable products that have been dietary staples since the beginning of civilization. One of the oldest and most ubiquitous of these products is beer, characterized by a low to moderate alcohol content and a complex flavor composed of bitter, sweet and aromatic elements. Beer is produced as a result of the fermentation by yeast of soluble carbohydrates, such as maltose and glucose, than have been produced by the enzymatic hydrolysis of starches originating in plant material, usually grains such as barley, wheat or corn, but can be from potatoes or other root crops. Flowers or cones from hop plants are added as bittering agents that also serve the dual purpose of being anti-bacterial. The anaerobic fermentation of the sugars by the yeast produces ethanol and carbon dioxide as major products but the yeast also affects flavor by the production of other flavor compounds, such as diketones, alcohols and esters in lesser amounts. The primary fermentation may be completed in a few days, while maturation of the beer may take several months. The particular style of beer is affected by the source of the carbohydrates (for example variety of barley malt), the variety and quantity of hops and other flavorings, the species and strain of yeast and the fermentation and maturation conditions employed by the brewer.

Since the late 19$^{th}$ century the ability to prepare and maintain pure yeast cultures has been one of the primary reasons for the vast improvement in beer quality worldwide. Beer styles have diverged over the past two hundred years into two main categories, ale and lager, their differences due primarily to the species of yeast used for fermentation, *S. cerevisiae* or *S. pastorianus*. Numerous strains of these two species have been selected by brewers to impart specific characteristics to their beer in an attempt to differentiate their products (Smart, K. (2003) *Brewing Yeast Fermentation Performance*, Editor 2$^{nd}$ ed., Blackwell Publishing, Oxford, UK). However, using this approach, innovation has been limited, especially in the European industry where many brewers are reluctant to deviate from the German Purity Law of 1516, in which ingredients for making beer were limited to barley, water and hops (yeast added as a fourth ingredient in the 19$^{th}$ century) (www.germanbeerinstitute.com/history.html).

In contrast to European tradition, in the 20$^{th}$ century, many American brewers began using alternative sugar sources (adjuncts), including corn and rice, and hops have been replaced or supplemented with many other flavor ingredients such as spices and fruit. However, other than the Belgian sour beers that typically rely on *Lactobacillus* spp. or *Pediococcus* spp. of bacteria or wild yeast from the genus *Brettanomyces* (Guinard, J-X. (1990) *Lambic*. Brewers Publications, Boulder Colo.), there have been no significant developments with respect to the use of alternative yeast species for producing new beer styles and flavors. Most yeast do not have the metabolic capabilities to be used in a practical beer fermentation. In particular, they do not have the ability to ferment maltose, they do not tolerate greater than a few percent alcohol, and when used they can produce undesirable flavors and aromas The present invention overcomes previous shortcomings in the art by providing methods employing newly identified yeasts for use in production of fermented beverages including alcoholic cider and malt beverages such as beer and for the production of lactic acid and biofuel.

SUMMARY OF THE INVENTION

One aspect of the invention provides a method of producing a fermented beverage, comprising: fermenting at least one carbohydrate in the presence of *Lachancea thermotolerans* to produce a fermented beverage.

A second aspect of the invention provides a method of producing a fermented beverage, comprising: fermenting at least one carbohydrate in the presence of *Lachancea thermotolerans* to produce a primary fermentation product; and maturing (secondary fermentation) the primary fermentation product to produce a fermented beverage.

A third aspect of the invention provides a method of producing a fermented beverage, comprising: fermenting at least one carbohydrate to produce a primary fermentation product; and maturing the primary fermentation product in the presence of *Lachancea thermotolerans* to produce a fermented beverage.

In a fourth aspect of the invention, a method of producing lactic acid is provided, comprising: fermenting at least one of starch, maltose, glucose, maltotriose and/or fructose in the presence of *Lachancea thermotolerans* to produce lactic acid.

In a fifth aspect of the invention, a method of fermenting carbohydrates at low pH is provided, comprising fermenting at least one carbohydrate in the presence of *Lachancea thermotolerans* under suitable conditions for a period of time sufficient to allow fermentation of at least a portion of said at least one carbohydrate.

Further provided herein are novel isolated yeast strains and products produced by the methods of the invention including malt beverages (e.g., beer, lager, ale, and sour style), alcoholic cider, lactic acid and biofuel.

These and other aspects of the invention are set forth in more detail in the description of the invention below.

BRIEF DESCRIPTION OF THE DRAWINGS

FIG. 2 shows percent similarity of the ITS1-5.8SrRNA-ITS2 DNA sequence of Lachancea species and strains YB16 deposited as NRRL Y-67252 and/or strain BB202 deposited as NRRL Y-67253.

DETAILED DESCRIPTION

Figure 1:
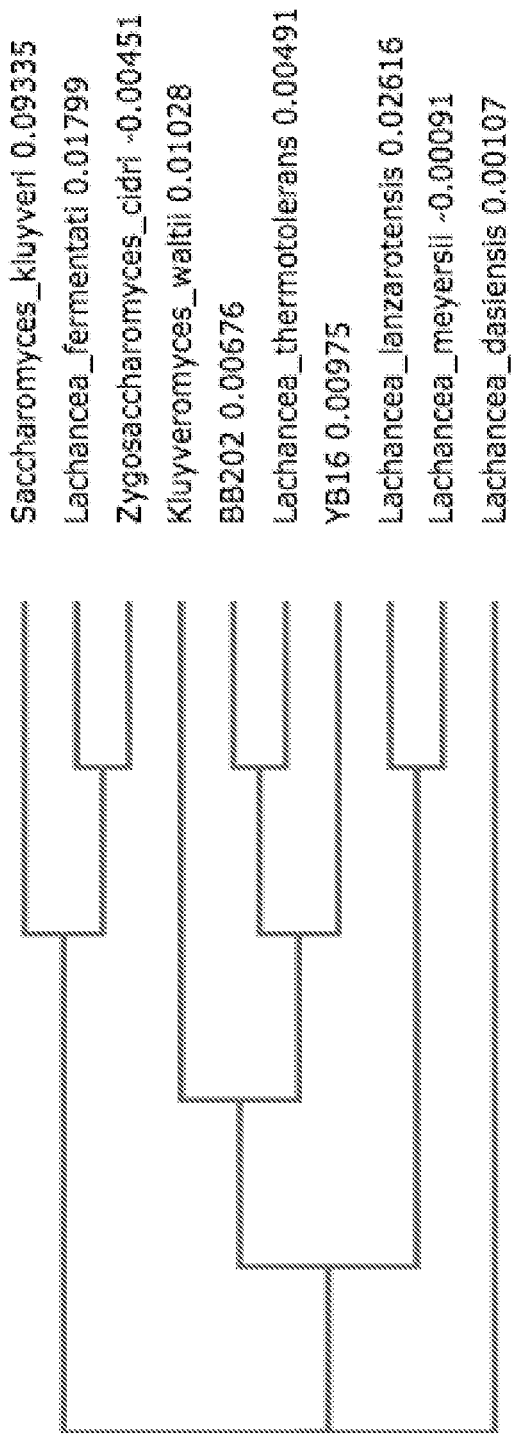
FIG. 1 shows a cladogram of *Lachancea* species based off of a multiple sequence alignment of the partial ITS1-5.8rRNA-ITS2 sequence.

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural fauns as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like refers to variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the terms "increase," "increasing," "increased," "enhance," "enhanced," "enhancing," and "enhancement" (and grammatical variations thereof) describe an elevation of at least about 25%, 50%, 75%, 100%, 150%, 200%, 300%, 400%, 500% or more as compared to a control.

As used herein, the terms "reduce," "reduced," "reducing," "reduction," "diminish," and "decrease" (and grammatical variations thereof), describe, for example, a decrease of at least about 5%, 10%, 15%, 20%, 25%, 35%, 50%, 75%, 80%, 85%, 90%, 95%, 97%, 98%, 99%, or 100% as compared to a control. In particular embodiments, the reduction can result in no or essentially no (i.e., an insignificant amount, e.g., less than about 10% or even 5%) detectable activity or amount.

As used herein, "fermenting," "fermentation" and grammatical variations thereof mean the production of alcohol and carbon dioxide from the breakdown of the carbohydrates by the yeast.

As used herein, "maturing," "maturation" and grammatical variations thereof mean the time following the fermentation when the yeast can continue to affect the flavor and aroma of the beverages through their metabolic activity. Other interchangeable terms for this process include "conditioning" or "secondary fermentation."

"Yeast species" as used herein refers to a recognized biological group as determined by the International Code of Botanical Nomenclature (see, Seifert and Rossman (2010) *IMA Fungus*. 1(2):109-116).

"Yeast strain" as used herein refers to a taxonomic grouping which is one lower than species. These are unique, or putatively unique, clones that may vary from one another in genotype and phenotype, but are still more closely related to one another (as a species group), than to the strains of another species.

"Type strain" as used herein refers to the living reference strain for valid species (per Kyrpides et al. (2014) Genomic Encyclopedia of Bacteria and Archaea: Sequencing a myriad of type strains. *PLoS Biol* 12(8):e1001920. Doi:10.1371/journal.pbio.1001920).

Beer styles have diverged over the past two hundred years into two main categories, ale and lager, their differences due primarily to the species of yeast used for fermentation, *S. cerevisiae* or *S. pastorianus*. Typically, ale is fermented at room temperatures (18° C.-24° C.) by *S. cerevisae* with short maturation times (typically 10-30 days) and the beer characterized by some residual sweetness and moderate to high bitterness. In contrast, lagers are fermented at cellar temperatures (8° C.-14° C.) by *S. pastorianus* with long maturation times (4-12 weeks), and the beer characterized by minimal residual sweetness and low to moderate bitterness.

Belgian sour-style beer, referred to as lambic or gueuze, is produced by mixed culture fermentations of wort that, in addition to barley malt, usually contains some wheat and/or fruit and aged (oxidized) hops. The culture responsible for the fermentation is often based on the local cultures found within the specific brewery environment and may be composed of species from the genera of *Saccharomyces, Brettanomyces, Dekkera, Kloeckera, Pediococcus* and *Lactobacillus* (Guinard 1990). The fermentations for sour-style beers are for extended times, typically several months to 2 years for traditional lambics. This type of beer is characterized by high levels of organic acids (mainly lactic and acetic with lesser amounts of propionic, isobutyric and butyric) with a pH ranging between 3.3 to 3.9. Ethyl acetate is also found at elevated levels in these beers, adding to the vinegar odor. The unique composition of the wort, combined with the variety and types of microbes used as well as the long fermentation times, results in very different flavor profiles from that of standard ales and lagers.

The present invention is directed to yeast species and strains newly identified for use in preparing fermented beverages, such as beer, thereby providing the brewer the ability to produce fermented beverages having new and distinctive flavor and aroma characteristics as compared to fermented beverages produced using the standard yeast species such as *S. cerevisiae* and *S. pastorianus*.

Specifically, work by the present inventors has shown that insects, such as wasps, bees and ants, can harbor diverse yeasts that have unexpected metabolic capabilities that make them useful for various human applications, including beer brewing and other fermentation processes.

In general, the present invention provides a process of yeast isolation and characterization involving homogenization of host insect material and using various selection media to foster the growth of yeasts. Initial selection and purification of yeast strains is based on cell and colony morphologies consistent with each microbial group. The identification of the yeast species may be determined by sequencing a genetic 'fingerprint' gene of these strains, followed by sequence comparison with a public repository of such genes (GenBank®). This standard method of species identification includes the procedural steps of genomic DNA isolation, purification, and then ITS1-5.8S-ITS2 (or D1/D2 LSU) rDNA amplification, followed by Sanger DNA sequencing. Those yeasts that are within the food-safe order of true yeasts (Order: *Saccharomycetales*) can be subsequently assessed biochemically. Physiological screening for maltose fermentation—a necessary metabolism for successful brewing yeasts—may be used as an initial assessment by inoculating yeast in phenol red base broth plus maltose with durham tubes. Candidate yeast species and strains can be selected that show promise for brewing based on the results of these tests and screened more fully for brewing capability. Using these methods many new yeast species and strains useful in the brewing of fermented beverages may be identified.

In some embodiments, the yeast is one that is isolated from a bumblebee or a wasp. Thus, the invention provides a method of producing a fermented beverage, comprising: fermenting at least one carbohydrate (e.g., grain, vegetable, malt, wort, corn syrup, sugar cane, fruit, fruit juice, honey, and/or molasses) in the presence of a yeast isolated from a bumblebee or a wasp under suitable conditions for a period of time sufficient to produce a fermented beverage. In some embodiments, the fruit is not grape and/or the fermented beverage is not wine.

In some embodiments, a yeast useful for producing a fermented beverage can be *Lachancea thermotolerans*. In some embodiments, the yeast can be a strain of *L. thermotolerans*. In representative embodiments, the yeast strain can be YB16 (deposited as NRRL Y-67252) and/or BB202 (deposited as NRRL Y-67253).

Accordingly, one aspect of the invention provides a method of producing a fermented beverage, comprising: fermenting at least one carbohydrate (e.g., grain, vegetable, malt, wort, corn syrup, sugar cane, fruit and/or fruit juice, honey and/or molasses) in the presence of *L. thermotolerans* under suitable conditions for a period of time sufficient to produce a fermented beverage. In some embodiments, the at least one carbohydrate is not grapes and/or the fermented beverage is not wine.

A further aspect of the invention provides a method of producing a fermented beverage, comprising: fermenting at least one carbohydrate (primary fermentation) in the presence of *L. thermotolerans* under suitable conditions for a period of time sufficient to produce a primary fermentation product; and maturing the primary fermentation product (secondary fermentation) to produce a fermented beverage. In some embodiments, the at least one carbohydrate is not grapes and/or the fermented beverage is not wine.

In an additional aspect of the invention, a method of producing a fermented beverage is provided, comprising: fermenting at least one carbohydrate to produce a primary fermentation product; and maturing the primary fermentation product in the presence of *L. thermotolerans* under suitable conditions for a period of time sufficient to produce a fermented beverage. Thus, in some aspects, other yeast species (e.g., traditional yeast species such as *Saccharomyces* spp.) can be used in fermenting, and *L. thermotolerans* can be used for maturing the primary fermentation product. In some embodiments, the at least one carbohydrate is not grapes and/or the fermented beverage is not wine.

In representative embodiments, the *L. thermotolerans* strain can be YB16 (deposited as NRRL Y-67252) and/or BB202 (deposited as NRRL Y-67253). Thus, in some embodiments, a method of producing a fermented beverage is provided, comprising: fermenting at least one carbohydrate in the presence of strain YB16 (deposited as NRRL Y-67252) and/or strain BB202 (deposited as NRRL Y-67253) under suitable conditions for a period of time sufficient to produce a fermented beverage. In a further aspect, a method of producing a fermented beverage is provided, comprising: fermenting at least one carbohydrate (primary fermentation) in the presence of strain YB16 (deposited as NRRL Y-67252) and/or strain BB202 (deposited as NRRL Y-67253) under suitable conditions for a period of time sufficient to produce a primary fermentation product; and maturing the primary fermentation product (secondary fermentation) to produce a fermented beverage. In an additional aspect of the invention, a method of producing a fermented beverage is provided, comprising: fermenting at least one carbohydrate to produce a primary fermentation product; and maturing the primary fermentation product in the presence of strain YB16 (deposited as NRRL Y-67252) and/or strain BB202 (deposited as NRRL Y-67253) under suitable conditions for a period of time sufficient to produce a fermented beverage, wherein other yeast species (e.g., *Saccharomyces* spp.) can be used in fermenting, and YB16 or BB202 can be used for maturing the primary fermentation product.

In some embodiments, a combination of yeasts may be used in the fermenting and/or maturing steps. Thus, in some embodiments, a method is provided comprising fermenting at least one carbohydrate in the presence of yeast, wherein the yeast comprises, consists essentially of, or consists of *L. thermotolerans* strains YB16 and/or BB202, and may further comprise *Saccharomyces cerevisiae* and/or *Saccharomyces pastorianus*, to produce a primary fermentation product; and maturing the primary fermentation product (secondary fermentation) to produce a fermented beverage. In other embodiments, a method of producing a fermented beverage is provided, comprising: fermenting at least one carbohydrate to produce a primary fermentation product; and maturing the primary fermentation product in the presence of yeast, wherein the yeast comprises, consists essentially of, or consists of *L. thermotolerans* strains YB16 and/or BB202, and further comprises *S. cerevisiae* and/or *S. pastorianus*, to produce a fermented beverage. In some embodiments, the at least one carbohydrate is not grapes and/or the fermented beverage is not wine.

In some embodiments, the invention provides a method for producing mead, comprising fermenting honey in the presence of *L. thermotolerans* under suitable conditions for a period of time sufficient to produce a fermented beverage. In representative embodiments, the invention provides a method for producing mead, comprising: fermenting honey in the presence of yeast strain YB16 and/or yeast strain BB202 under suitable conditions for a period of time sufficient to produce mead.

In some embodiments, a fermented beverage can be beer, including but not limited to, ale or lager. In some embodiments, the ale or lager can be sour-style beer. In some embodiments, the lager can be sour-style beer (e.g., when the fermentation occurs at a low temperature). In some embodiments, the fermented beverage can be alcoholic cider or mead (e.g., fermenting honey). In other embodiments, the fermented beverage can be wine or it can be mead. In further embodiments, the fermented beverage is not wine. Methods for brewing these and other different types of fermented beverages are known in the art.

The fermented beverage brewing process comprises, in general, malting, mashing, lautering, boiling, fermenting, maturing (conditioning), filtering and packaging. As understood by those of skill in art, some of these steps can be skipped and others added, as well as steps can be modified to achieve the particular desired fermented beverage.

Fermentation to produce a beverage can comprise (1) a primary fermentation in which the yeast ferment the at least one carbohydrate selected by the brewer to produce a primary fermentation product, and (2) a maturing step (i.e., secondary fermentation, conditioning or aging), which allows the fermentation process to continue acting on the primary fermentation product, typically in the presence of a reduced and/or modified yeast population. The maturing process can be carried out under the same or different conditions (e.g., temperature) than that used for the fermenting step. Thus in some embodiments, a change in the temperature as compared to the primary fermentation step can be an increase or decrease in temperature. Furthermore, in some embodiments, the production of a fermented beverage can comprise a primary fermenting step but not a maturing step. Instead, the process may be complete and the fermented beverage produced after the fermenting step.

In some embodiments, the step of fermenting at least one carbohydrate may be carried out for about 1 day to about 30 days (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days and the like, or any range or value therein). In other embodiments, the step of fermenting at least one carbohydrate may be carried out for about 2 days to about 30 days (e.g., about 2, 3, 4, 5, 6, 7, 8, 9, 10, 11, 12, 13, 14, 15, 16, 17, 18, 19, 20, 21, 22, 23, 24, 25, 26, 27, 28, 29, 30 days and the like, or any range or value therein). In a representative embodiment, the step of fermenting at least one carbohydrate may be carried out for about 2 days to about 21 days (e.g., about 2, 3, 4, 5, 6, 7, 8, 9, 10, 11, 12, 13, 14, 15, 16, 17, 18, 19, 20, 21 days and the like, or any range or value therein). In some embodiments, the step of fermenting carbohydrates may be carried out at a temperature of about 4° C. to about 24° C. (e.g., about 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C. and the like, or any range or value therein). In some embodiments, the step of fermenting at least one carbohydrate may be carried out at temperature of about 8° C. to about 14° C. or about 18° C. to about 24° C. Any combination of temperature and time for fermenting the at least one carbohydrate can be chosen by the brewer.

Similar to the choice of time and temperature for fermenting at least one carbohydrate, the selection of temperature and time for maturing the primary fermentation product depends on the type of beer and the characteristics of the beer desired by the brewer.

For example, when producing lagers, generally the temperature is reduced in the maturing step as compared to the fermenting step. When producing ales, the temperature chosen for maturing may be about the same or may be lower than that for the fermenting step and for sour-style beers, the temperature for maturing can be highly variable. Thus, in some embodiments, maturing may be carried out at a temperature of about 1° C. to about 24° C. (e.g., about 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C. and the like, or any range or value therein). In some embodiments, the time period for maturing can be from about 10 minutes to about 16 weeks (e.g., 10 min, 11 min, 12 min, 13 min, 14 min, 15 min, 16 min, 17 min, 18 min, 19 min, 20 min, 21 min, 22 min, 23 min, 24 min, 25 min, 26 min, 27 min, 28 min, 29 min, 30 min, 35 min, 40 min, 45 min, 50 min, 55 min, 1 hr, 1.5 hr, 2 hr, 2.5 hr, 3 hr, 3.5 hr, 4 hr, 4.5 hr, 5 hr, 5.5 hr, 6 hr, 6.5 hr, 7 hr, 7.5 hr, 8 h, 9 hr, 10 hr, 11 hr, 12 hr, 15 hr, 18 hr, 22 hr, 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks and the like, or any range or value therein). In additional embodiments, the time period for maturing can be from about 2 days to 21 days (3 weeks) (e.g., about 2, 3, 4, 5, 6, 7, 8, 9, 10, 11, 12, 13, 14, 15, 16, 17, 18, 19, 20, 21 days and the like, or any range or value therein), or about 10 days to about 12 weeks (e.g., about 10 days, 11 days, 12 days, 13 days, 2 weeks, 3 weeks, 4 weeks, 5, weeks, 6, weeks, 7, weeks, 8 weeks, 9, weeks, 10, weeks, 11 weeks, 12 weeks and any range or value therein). In other embodiments, the time period for maturing can be up to about 3 months. In other embodiments, the time period for maturing a sour-style beer and/or an ale can be, for example, for about 2 days to about 30 days (e.g., about 2, 3, 4, 5, 6, 7, 8, 9, 10, 11, 12, 13, 14, 15, 16, 17, 18, 19, 20, 21, 22, 23, 24, 25, 26, 27, 28, 29, 30 days, or any range or value therein). In further embodiments, the time period for maturing can be about 4 weeks to about 12 weeks, for example, for maturing a lager beer. As the skilled artisan would be aware, a brewer can select any combination of temperature and time for maturing the primary fermentation product with the choice being determined by the desired characteristics for the fermented beverage being brewed (e.g., aroma, flavor, foam stability, acidity, alcohol content and mouth feel).

Notably, the use of *L. thermotolerans* in the fermenting and/or maturing steps of this invention surprisingly allowed the production of a sour-style beer in much less time than is typical for producing these types of fermented beverages. Thus, in a representative embodiment, a sour-style beer of the present invention can be made in about 3 days to about 12 weeks (e.g., about 3 days, 4 days, 5 days, 6 days, 1 week, 2 weeks, 3 weeks, 4 weeks, 5 weeks, 6 weeks, 7 weeks, 8 weeks, 9 weeks, 10 weeks, 11 weeks, 12 weeks, or any range or value therein). In contrast, using yeast and bacterial species standard in the art (e.g., *Saccharomyces* spp., *Brettanomyces* spp., *Dekkera* spp., *Kloeckera* spp., *Pediococcus* spp. and *Lactobacillus* spp.), the time period needed to produce a sour-style beer is about 6 months to about 2 years.

The source of the at least one carbohydrate for fermenting in the process of producing a fermented beverage is an important determinant in the strength and flavor of the resultant beverage. Any carbohydrate source that can be fermented by the yeast that produces the desired fermented beverage characteristics can be used. In some embodiments, the at least one carbohydrate can be any starch source. In some embodiments, the at least one carbohydrates can be grain, including, but not limited to, barley, rye, wheat, corn, sorghum, rice, or any combination thereof. In some embodiments, the at least one carbohydrate can be a vegetable, for example, a root vegetable, including, but not limited to, potato, cassava, sugar beet, or any combination thereof. In some embodiments, the at least one carbohydrate can be any fruit and/or fruit juice containing fructose, glucose and/or sucrose including, but not limited to, apple, strawberry, black current, cherry, raspberry, blackberry, blueberry, citrus (e.g., orange, lemon). In some embodiments, when fruit juice is the at least one carbohydrate, the fruit juice does not comprise added preservatives (e.g., sodium benzoate). In some embodiments, the fruit juice can be unfiltered, organic, and/or pasteurized. In some embodiments, the at least one carbohydrate can be starch, malt, wort, corn syrup, sugar cane, molasses, honey, and/or any combination thereof. Of course, any combination of carbohydrate sources can be used in the fermenting step, including, but not limited to, combinations of any grain, vegetable, malt, wort, corn syrup, sugar cane, fruit and/or fruit juice, honey, and/or molasses. Exemplary malts include 2-row, Black Patent, English Pale, Scottish Crystal, CaraVienne, Pilsner, Special Roast, Caramel, Carapils, Chocolate, Victory, Vienna, Munich, Weizen and/or any combination thereof. In representative embodiments, the at least one carbohydrate for use in producing a fermented beverage is not a grape or grape juice (i.e., the at least one carbohydrate is not from *Vitis vinefera*).

In additional embodiments, the method of producing a fermented beverage further comprises adding at least one (i.e., one or more, 1, 2, 3, 4, 5, 6, 7, 8, 9, 10, or more) flavoring in any step prior to fermenting, during and/or after fermenting in the methods of producing a fermented beverage. Any flavoring or combination of flavorings may be used that impart the flavor and aroma desired by the brewer. Further, when more than one flavoring is added, some may be added prior to fermenting and some may be added after fermenting. In some embodiments, a flavoring can include, but is not limited to, flowers (e.g., hops, hibiscus, rose, lavender), fruit (e.g., puree and/or extract of apple, pear, peach, apricot, plum, orange, cherry, raspberry, strawberry, banana, and the like), spices (e.g., coriander, ginger, vanilla, citrus peel, nutmeg, allspice, peppercorn), nuts (e.g., hazelnut), chocolate, honey, rose water and the like, and/or any combination thereof.

In some embodiments, the at least one flavoring can be hops. Any type of hops can be used and the choice will depend on the desired characteristics (e.g., bittering, aroma and flavor) of the fermented beverage being brewed. In some embodiments, the hops can include, but is not limited to, Amarillo, Bravo, Calypso, Centennial, Glacier, Greenburg, Nugget, Sterling, Hallertau, Tetnanger, Saaz, Cascade, Tomahawk, Fuggles, Tillicum, Zythus, Admiral, Phoenix, Herald, Hallertauer, Magnum, Perle, Tettnang, Spalt, Topaz, Motueka, Pacifica, Aramis, Junga, Sladek Sorachi Ace, and/or any combination thereof.

A further aspect of the invention is production of lactic acid using *L. thermotolerans*. Microbial fermentation to produce lactic acid is generally carried out using bacterial species, such as *Lactobacillus* spp.; however, these species have limitations. For instance, these bacteria are not tolerant of low pH, specifically pH below 5 (Porro et al. *Appl. Environ. Microbiol.* 65(9):4211-4215 (1999)). Thus, the process requires other chemical input during fermentation to maintain a higher pH. This leads to later purification issues when reclaiming the lactic acid. Filamentous fungi such as *Rhizopus* species have been used in addition to bacteria, but their filamentous morphology clogs fermentation tanks, making them poor candidates for production. Yeasts, such as *Saccharomyces*, can withstand lower pH and are single-cell organisms but they do not produce lactic acid naturally. Considerable effort has been put into genetically engineering yeast to produce lactic acid. However, the genetically engineered yeasts can have undesirable metabolic changes that result in poor performance and may be limited in use due to restrictions on the use of such genetically modified organisms.

*L. thermotolerans* has been shown to produce lactic acid in sequential or mixed fermentation (Benito et al. *Molecules* 20:9510-9523 (2015)) and Gobbi et al. *Food Microbiolog* 33:271-281 (2013)). However, the present inventors have surprisingly found that the *L. thermotolerans* strains YB16 and BB202 can produce lactic acid in single culture at substantially greater amounts than that produced by other *L. thermotolerans* strains such as ATCC 56472 (NRRL Y-8284).

Thus, another aspect of the invention provides a method of producing lactic acid, comprising: fermenting at least one of starch, maltose, glucose, maltotriose and/or fructose in the presence of *L. thermotolerans* under suitable conditions for a period of time sufficient to allow fermentation of at least a portion of the at least one of maltose, glucose, maltotriose and or fructose to lactic acid, thereby producing lactic acid. In some embodiments, the amount of lactic acid produced can be at least about 4 g/L to about 8 g/L (e.g., about 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8 g/L or greater and any value or range therein). In representative embodiments, the amount of lactic acid produced can be at least about 5.5 g/L to about 7.6 g/L or at least about 6 g/L to about 7.6 g/L. In some embodiments, the *L. thermotolerans* strain is YB16 and/or BB202.

Carbohydrates that *L. thermotolerans* can utilize for production of lactic acid also include, but are not limited to, those used in producing a fermented beverage. Thus, the at least one carbohydrate for use in producing lactic acid can include, but is not limited to, starch, grain, vegetable, malt, wort, corn syrup, sugar cane, fruit and/or fruit juice, honey, molasses, and/or any combination thereof as described herein. Typically, for production of lactic acid using *L. thermotolerans*, the temperature conditions can be similar to those for producing a fermented beverage (e.g., about 4° C. to about 24° C.) but can include higher temperatures (e.g., up to about 30° C.). In some embodiments, the fermentation time for production of lactic acid can be shorter than the time for fermentation to produce a fermented beverage. For example, the step of fermenting at least one carbohydrate for production of lactic acid may be carried out for about 1 day to about 5 days (e.g., about 1, 2, 3, 4, 5 days and the like, or any range or value therein).

In additional aspects, the invention provides a method of fermenting carbohydrates at low pH (e.g., at least about pH 4.2 or lower; e.g., about 4.2, 4.1, 4, 3.9, 3.8, 3.7, 3.6, 3.5, 3.4, 3.3, 3.2, 3.1, 3, and the like, or any range or value therein) comprising fermenting at least one carbohydrate in the presence of *L. thermotolerans* under suitable conditions for a period of time sufficient to allow fermentation of at least a portion of said at least one carbohydrate. In representative embodiments, the low pH is at least about pH 3.3. In some embodiments, the fermentation of the at least a portion of said at least one carbohydrate at low pH produces biofuel, wherein the biofuel is ethanol. In some embodiments, the at least one carbohydrate can be a high gravity substrate (i.e., concentrated), therefore allowing for higher ethanol concentrations to be produced, thereby reducing distillation costs. Further, the use of continuous ethanol production can increase volumetric productivity (g ethanol/L-hour).

In contrast to the production of fermented beverages, fuel ethanol production may be a more rapid fermentation. For example, the fermentation for fuel ethanol production may be carried out over days rather than weeks (e.g., 1, 2, 3, 4, 5, 6, 7, 8 days, and the like). The temperature range for fermentation for fuel ethanol production can be varied but typically is in the range of about 20° C. to about 30° C. (e.g., 20° C., 21° C., 22° C., 23° C., 24° C., 25° C., 26° C., 27° C., 28° C., 29° C., 30° C., and any range or value therein). In particular embodiments, the temperature range for fermentation for fuel ethanol production using *L. thermotolerans* can be about 25° C. to about 30° C. Moreover, while any starch can be used as the carbohydrate source for fuel ethanol production, a liquid containing a high concentration of sugar (e.g., 3-4 times that which is found in brewer's wort) is typically utilized. In some embodiments, the concentration of sugars for fermentation to produce fuel ethanol can be about 100 to 350 grams per liter (e.g., 100, 125, 150, 175, 200, 225, 250, 275, 300, 325, 350, and any range or value therein).

In some embodiments, the at least one carbohydrate for production of fuel ethanol can be any starch source. Thus, in some embodiments, the at least one carbohydrate can be starch; grain; vegetable; sugar cane; molasses; and/or any combination thereof. In representative embodiments, the at least one carbohydrate can be sugars can be derived from corn or sugar cane.

Under the conditions of low pH and high sugar concentration, *L. thermotolerans*, for example, strain YB16 and/or BB202, can provide a high concentration of ethanol (at least about 10% to about 18% v/v). Further in contrast to beverage fermentation, the conditions for fuel ethanol production are carried out under relatively non-aseptic conditions that can be susceptible to bacterial contamination. In beverage fermentation, care is taken in equipment and practices to minimize the potential for contamination and the resultant ethanol concentration is much lower than that in fermentation for fuel ethanol production.

*L. thermotolerans* is advantageous over standard *S. cerevisiea* in biofuel production because *L. thermotolerans* can produce ethanol at a low pH (at least about pH 4.2 or lower), it can produce lactic acid itself, and because the acid produced by *L. thermotolerans* can act as a natural deterrent against contaminants to the fermentation process. A comparative yeast, *S. cereviseae*, does not produce lactic acid. Strains BB202 and YB16 are advantageous over strain NRRL Y-8284 in that they can produce more ethanol and can produce the ethanol from malt. In representative embodiments, the amount of ethanol produced when fermenting at least one carbohydrate at low pH in the presence of *L. thermotolerans*, for example, in the presence of strains BB202 and YB16, can be at least about 10% to about 18% ethanol by volume.

In additional aspects, the present invention provides a fermented beverage produced by any method of this invention. In some embodiments, the fermented beverage of the invention is beer. In some embodiments, the fermented beverage of the invention is lager. In other embodiments, the fermented beverage is ale. In further embodiments, the fermented beverage is sour-style beer comprising a pH of about 3.0 to about 4.5. In some embodiments, a sour-style beer of the invention comprises lactic acid and acetic acid produced during the brewing process (that is, lactic acid is not added). In a further embodiment, a sour-style beer of the invention comprises esters, acetate esters, ethyl acetate, isoamyl acetate, phenylethyl acetate, medium chain fatty acid ethyl esters, ethyl hexanoate, ethyl octanoate, or any combination thereof. In some embodiments, a fermented beverage can be alcoholic cider. In other embodiments, a fermented beverage of the invention can be wine or mead. In particular embodiments, a fermented beverage of the invention is not wine.

In still further aspects, the preset invention provides ethanol and lactic acid produced by any of the methods described herein.

Also provided are isolated yeast strains, YB16, deposited as NRRL Y-67252 and BB202, deposited as NRRL Y-67253.

Deposit of Biological Material

Yeast strain BB202 (NCSU) was deposited on May 6, 2016, under the provisions of the Budapest Treaty in the Agricultural Research Culture Collection (NRRL) in Peoria, Ill., and has been assigned Accession No. NRRL Y-67253. Yeast strain YB16 was deposited on May 6, 2016, under the provisions of the Budapest Treaty in the Agricultural Research Culture Collection (NRRL) 1815 N. University Street, Peoria, Ill. 61604, and has been assigned Accession No. NRRL Y-67252.

The deposits will irrevocably and without restriction or condition be available to the public upon issuance of a patent. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. § 112. However, it should be understood that the availability of a deposit does not constitute a license to practice the subject invention in derogation of patent rights granted by government action. The deposit will be maintained without restriction in the NRRL Depository, which is a public depository, for a period of 30 years, or 5 years after the most recent request, or for the enforceable life of the patent, whichever is longer, and will be replaced if it ever becomes nonviable during that period.

The invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

EXAMPLES

Example 1. Strain Isolation

Yeast strains were obtained from social insects by culturing and isolating them on Potato Dextrose Agar (PDA) and Maltose Extract Agar (MEA). Plates were incubated at about 30° C. Following isolation in pure culture, two strains (designated YB16 (from paper wasp) (deposited as NRRL Y-67252) and BB202 (from bumblebee) (deposited as NRRL Y-67253), were passaged less than five times before they were provided for fermentation seed cultures.

Example 2. Strain Species Identification

The yeast strains were identified to species by a partial ITS1-5.8SrRNA-ITS2 DNA sequence comparison—the standard molecular identification method for assigning fungal taxonomy (see, Schoch et al., The Fungal Barcoding Consortium. (2012) PNAS. 109(16):6241-6246). This about 650 bp fragment was amplified from pure cultures of these strains. The specific gene fragment of interest was amplified using the universal fungal primers Pn3 (CCGTTGGT-GAACCAGCGGAGGGATC) and Pn34 (TGCCGCTT-CACTCGCCGTT) (Viaud et al. (2000) *Mycol. Res.* 9:1027-1032). Briefly, whole cells were added to 25 µl PCR cocktails containing: 12.5 µl Promega Gotaq® PCR master mix, 0.6 µM primers, 5 µl sample genomic DNA, 4 µl water. PCR was run on a thermocycler (model 2700, GeneAmp® PCR System, Applied Biosystems), with the cycling parameters of 95° C. 60 s, 50° C. 90 s, 72° C. 60 s for 30 cycles. Amplified sequences were purified and sequenced (Sanger sequencing) using the amplification primers).

The resultant forward read of strain BB202 was manually trimmed at the ends to assure quality of the final sequence, while a consensus contig of the forward and reverse read was constructed for strain YB16. Final sequences were compared with those sequences in the GenBank repository using the BLAST® nucleotide algorithm using only Type sources for comparison (Altschul et al. (1990) *J. Mol. Biol.* 215:403-410).

To compare these strains with those of *Lachancea thermotolerans*, and the closest sister species, sequences of the ITS of Type strains of *Kluyveromyces* (*Lachancea*) *waltii*, *L. thermotolerans*, and *L. meyersii*, *L. dasiensis*, *L. lanzarotensis*, *L. fermentati*, and *Zygosaccharomycs* (*Lachancea*) *cidri*, were downloaded from GenBank®. A multiple alignment and cladogram were constructed and visualized in CLUSTAL O (1.2.1) using default parameters (Sievers et al. (2011) *Molecular Systems Biology.* 7:539; doi:10.1038/msb.2011.75).

The species identification of strains YB16 and BB202 was further confirmed by comparisons of genetics, cell and colony morphologies, temperature ranges of growth, and the utilization of various carbon compounds (as is standard in the field) by the Fungal Testing Laboratory of the University of Texas Health Science Center.

Example 3. Strain Metabolic Characterization

Maltose fermentation capability of the strains was assessed using a standard phenol red broth plus maltose assay. A colony of each strain growing on PDA was inoculated into separate broths. Following 48 hours of incubation at about 25° C., a yellow, turbid culture, and the presence of air in the durham tube were positive indicators of maltose fermentation. Literature values were recorded for the *Lachancea* Type strains (*The Yeasts: A taxonomic Study*, Volume 1 ed. Cletus Kurtzman, J W Fell, eun Boekhout. Elsevier, London 2011).

Example 4. Fermentation Performance

Two strains of *L. thermotolerans*, YB16 and BB202, were tested for their fermenting ability using brewer's wort prepared from 100% barley malt in the NCSU Research Microbrewery. The brewer's wort was prepared in a 200 L mash tun by the addition of about 60 kg of malted barley, previously ground in a roller mill, to 170 L of water at 54° C., thereby constituting the mash. Over the next 60 minutes the mash was stirred and heated gradually to 72° C. to accomplish the enzymatic hydrolysis of the starches and proteins in the malted barley. After raising the temperature to 76° C. to de-activate the enzymes, the liquid was drained from the mash tun through a false bottom mesh, leaving the grain residue behind. This liquid constituted the wort, that was subsequently boiled for 90 minutes with various additions of hop pellets. The fermentations were carried out at three different scales, 1 liter flasks (400 mL working volume), 20 L conical fermenters and at approximately 100 L in 2.5 bbl Unitanks. The fermentations were carried out for different times ranging from 10 days to 3 weeks and at different temperatures, controlled between 18 and 22° C. The extent and number of analyses of fermentation samples varied between experiments, and included cell counts, specific gravity (SG), and measures of ethanol, maltose, glucose, glycerol, pH, and a variety of flavor compounds by GC-MS. Various batches were also evaluated for consumer acceptance at a number of social events held both on and off the NCSU campus.

Example 5. Results

Strains YB16 and BB202 were identified as *L. thermotolerans* based on ITS sequence similarity to the Type strain of *L. thermotolerans*, as well as the greater DNA sequence dissimilarity between these strains and the other *Lachancea* species (FIGS. 1-2). FIG. 1 provides a cladogram of *Lachancea* species based off of a multiple sequence alignment of the partial ITS1-5.8rRNA-ITS2 sequence. This cladogram is generally consistent with trees constructed using the D1/D2 LSU phylogenetic marker of *Lachancea* spp. (Kurtzman et al 2011). FIG. 2 shows the percent similarity of ITS1-5.8SrRNA-ITS2 of *Lachancea* species and the two *L. thermotolerans* strains YB16 and BB202.

Strain Morphological and Physiological Characterization.

Colony morphology of YB16 and BB202 are consistent with *L. thermotolerans*, with circular colonies appearing butyrous, glossy, and cream colored after approximately three days growth on PDA. The two strains were tested for their ability to ferment maltose, which is one component of the ability to make palatable beer. YB16 and BB202 fermented maltose within 48 hours of inoculation at about 25° C., consistent with the variable maltose fermentation capability of *L. thermotolerans*, but not by the closest relative, *L. waltii* (Table 1).

TABLE 1

Maltose fermentation by *L. thermotolerans* and environmental isolates

| | |
|---|---|
| YB16[a] | + |
| BB202[a] | + |
| *Lachancea thermotolerans* Type Strain[b] | v |
| *Lachancea waltii* Type Strain[b] | − |

[a]This study
[b]Reference values (*The Yeasts: A taxonomic Study*, Volume 1 ed. Cletus Kurtzman, JW Fell, eun Boekhout. Elsevier, London 2011)
"+" means positive;,
"−" means negative; and
"v" means variable.

Confirmation of Species Identification

The Fungal Testing Laboratory of the University of Texas Health Science Center confirmed that YB16 and BB202 are strains of the species *L. thermotolerans* based on their standard analysis. The results provided in Table 2 are consistent with those for *L. thermotolerans*.

TABLE 2

Summarized results from the Fungal Testing Laboratory of the University of Texas Health Science Center concluding that strains YB16 and BB202 are of the species *Lachancea thermotolerans*

| Fermentation comparison | | | |
|---|---|---|---|
| Carbon | Type Strain** | YB16* | BB202* |
| Glucose | + | + | Not performed |
| Galactose | v | − | Not performed |
| Sucrose | + | + | Not performed |
| Maltose | v | + | Not performed |
| Lactose | − | − | Not performed |
| Raffinose | + | + | Not performed |
| Tre | s | + | Not performed |
| Cel | Not Reported | − | Not performed |
| Mez | Not Reported | + | Not performed |
| Mel | Not Reported | − | Not performed |

| Growth Comparison on various carbon sources | | | |
|---|---|---|---|
| Carbon | Type Strain | YB16 | BB202 |
| Glucose | + | + | + |
| Sucrose | + | + | +/v |
| Raffinose | + | + | − |
| Galactose | v | + | + |
| Lactose | − | + | + |
| Trehalose | + | + | +/v |
| Maltose | + | + | +/v |
| Melezitose | + | + | +/v |
| Cellobiose | − | + | + |
| D-Xylose | − | − | − |
| L-Arabinose | − | − | − |
| Glycerol | + | + | + |
| N-Acetyl-D-glucosamine | − | − | + |
| Xylitol | + | + | + |
| 2-Keto-D-gluconate | v | +/v | + |
| Growth at 30° C. | + | + | + |
| Adonitol | Not reported | + | + |
| Inositol | Not reported | + | v |
| D-Sorbitol | Not reported | + | v |
| Methyl-alphaD-Mannopyranoside | Not reported | + | v |

| Temperature studies after five days growth on SDA | | |
|---|---|---|
| Temp | BB202 | YB16 |
| 30° C. | + | + |
| 35° C. | − | + |
| 42° C. | − | − |

| Microscopic morphology on corn meal Dalmau (at 25° C.) |
|---|
| BB202 and YB16 have Blastoconidia present |

| Colony morphology on SDA isolation plate at 30° C. after 24 growth |
|---|
| BB202 and YB16 have colonies that are moist, smooth, and cream colored |

| Molecular sequencing |
|---|
| BB202 and YB16 are consistent with *L. thermotolerans* |

*Data on YB16 and BB202 produced by the Fungus Testing Laboratory, University of Texas Health Science Center at San Antonio, Department of Pathology
**Data on type strain per reference values from: The Yeasts: A taxonomic study. Ed by Cletus Kurtzman, JW Fell, Teun Boekhout. Elsevier. 22011 Pag 516-517.

Fermentation performance.

Figure 3:
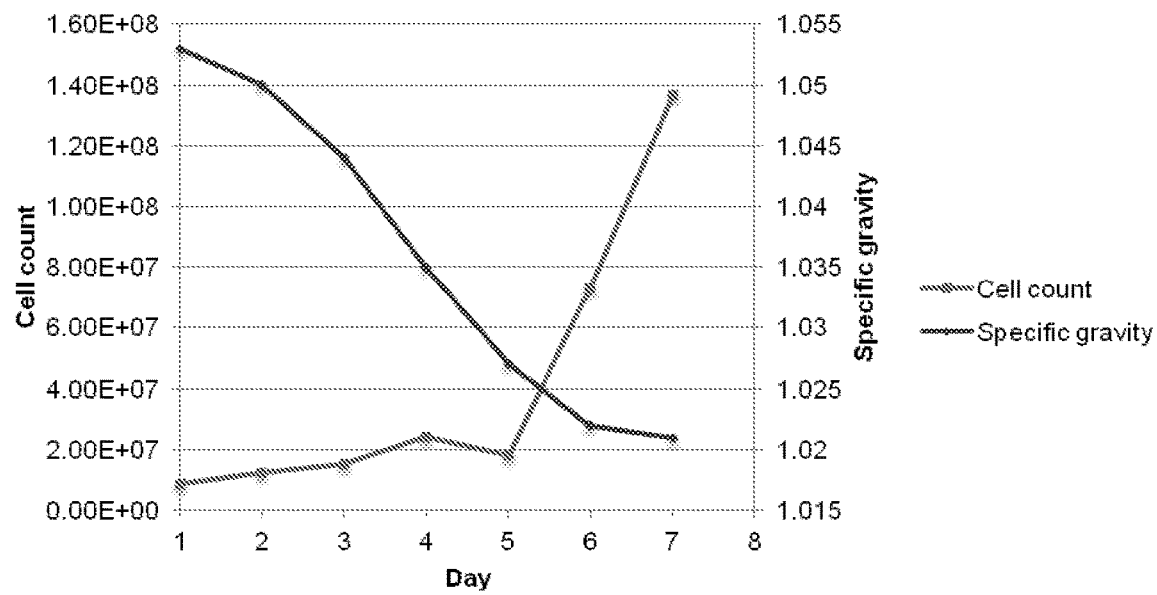
FIG. 3 shows the utilization of sugars and cell growth during fermentation at 22° C.

FIG. 3 shows average results from *L. thermotolerans* BB202 fermentation of IPA wort in triplicate 400 mL volume flasks, incubated at 22° C. Final gravity was achieved within 7 days, confirming the rate of fermentation to be comparable to the standard ale yeast, *S. cerevisiae*.

The final pH of beer produced by yeast BB202 is typically in the range 3.9 to 4.1, less acidic than some traditional sour beer which are in the range 3.0-3.5, but more acidic than standard ales and lagers (typically 4.2-4.8). The following table includes the specific acid detected in a beer produced by BB202 (Table 3).

TABLE 3

Acidic compounds detected in a beer produced by yeast BB202 from IPA wort fermented at 18° C.

Lactic acid
Acetic acid
Malic acid
Succinic acid

Figure 4:
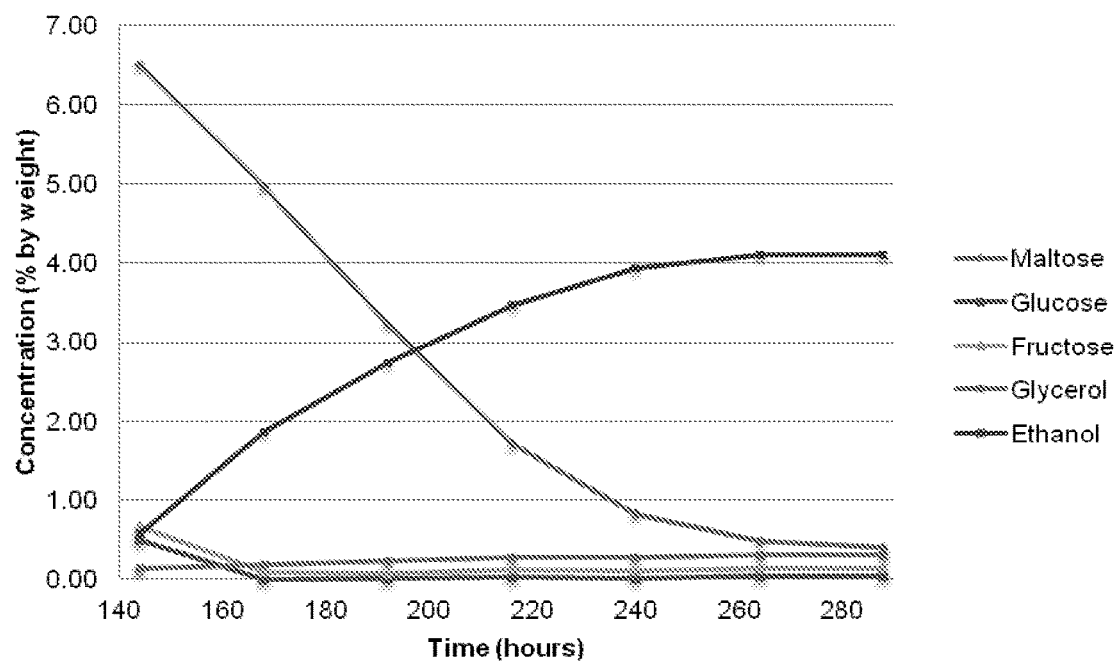
FIG. 4 shows sugar consumption and ethanol production by L. thermotolerans strain BB202 from the fermentation of IPA wort.

Sugar consumption and ethanol production and metabolic byproducts of a particular beer fermentation of BB202 using IPA wort is provided in FIG. 4 and Table 4. The fermentation of IPA wort was conducted at 18° C. in triplicate 400 mL volume flasks.

Table 4 shows exemplary metabolic byproducts identified in the beer produced by yeast strain BB202 using gas chromatography-mass spectrometry (GC-MS). Notably, the concentrations of these various components in any particular beer produced by BB202 will be affected by initial wort composition, fermentation temperature, and fermentation time. Here the wort used was IPA and the fermentation temperature was 18° C.

TABLE 4

Metabolic byproducts in the beer produced by yeast strain BB202

| Component | Effect on flavor profile |
|---|---|
| Ethyl acetate | Solvent, fruity, sweet |
| Ethanol | Warming, alcoholic |
| Isoamyl acetate | Fruity, banana |
| Isoamyl alcohol | Alcohol, banana |
| Phenylethyl acetate | Rose, honey, apple |
| Phenylethyl alcohol | Alcohol, flowery, honey-like |

*The concentrations of these various components in any particular beer produced by BB202 will be affected by initial wort composition.

Using the *L. thermotolerans* strains of this invention, three different beers were produced in sufficient quantity for taste evaluation by consumers. The first beer was produced in a 20 L quantity by yeast YB16 by fermentation of an IPA wort at 18° C. for 10 days. The beer was matured for an additional 10 days at 12° C. before filtering and carbonation. It was offered for consumer tasting at the International Beer Festival in Raleigh, N.C. on Apr. 5, 2014. The response of consumers was positive, especially among those that preferred sour-style beer. The second beer was produced, also in a 20 L quantity, by yeast BB202 by fermentation of a Blonde Ale wort for 5 days at 18° C., followed by 5 days of maturation at 12° C. and then filtering and carbonation. This beer was sweet, with significant residual sugar (53 g/L maltose) and only 1.8% ABV. The beer was served at the North Carolina Museum of Natural Sciences at a Science of Beer event held on Aug. 21, 2014. The beer was an instant sensation, many consumers believing that the beer had been made with the addition of honey, even though the wort was all-malt based. Thus, it appears that yeast strain BB202 imparts the flavor of honey without the extra cost of adding such an ingredient. The third variation was also produced using yeast BB202 by the fermentation of an amber ale wort, this time in Unitank fermenters with a 70 L liquid volume. The wort was fermented for 2 weeks at 18° C. and then matured at 6° C. for 3 days prior to filtering and carbonation. The residual sugar level was comparable to the standard amber ale (2-3 g/L maltose) with ethanol slightly below, at 4.2% ABV versus 5.6% ABV. This beer was served at various NCSU events between October, 2014 and January, 2015. The moderate acidity (pH of 4.0), combined with elevated citrus flavor and aroma proved to be very popular.

To the knowledge of the present inventors, no strains of *L. thermotolerans* have been proposed for beer brewing, nor does it appear that they are found as a contaminant in beer. However, the present invention has demonstrated the utility of these yeast in producing highly palatable malt beverages, specifically of the sour-style of beer, with varying flavor profiles, acidity and ethanol levels comparable to Belgian-style sour beers. The fermentations were carried out in both pure and mixed cultures of yeast, under standard ale fermenting conditions (18-22° C. for 1 to 3 weeks). This contrasts with the current production techniques for sour-style beers that utilize additions of acid-forming bacteria or wild yeast from the genus *Brettanomyces* spp, combined with very long fermentation times. Fermented beverages beverages produced using *Lachancea thermotolerans* have novel and distinctive flavor and aroma characteristics, while also adhering to the German purity law of using only barley malt, hops, water and yeast as raw materials.

Example 6. Use of *Lachancea thermotolerans* BB202 (NCSU) for the Production of Malt Beverages 1. Fermentation
1.1. Yeast Management In this study two strains of *Lachancea thermotolerans* were utilized. The first was a newly identified strain obtained from a bumblebee and isolated at North Carolina State University, denoted as *L. thermotolerans* strain BB202. The second, *L. thermotolerans* NRRL Y-8284, was obtained from the American Type Culture Collection (ATCC® #56472). Master glycerol stocks (250 μL of 50% glycerol in water solution with 1000 μL of yeast slurry) of both yeast strains were prepared and stored at −80° C. Yeast potato dextrose agar (YPDA) containing 1% yeast extract, 2% peptone, 2% dextrose, 1.5% agar (Sigma Aldrich, MO, U.S.A.) media was used to grow yeast cultures and was stored at 4° C. until use.

1.2. Wort Production

Wort was produced at the pilot scale, using a 2.5 BBL (1 BBL=117 L) mash tun and boil kettle (Diversified Metal Engineering Ltd., P.E.I., Canada). The barley malt was milled using a roller mill (Appolo Machine & Products Ltd., Saskatoon, Canada). For fermentations, two worts were created: a Pilsner wort for laboratory scale experiments and a Lambic wort for pilot scale experiments. The Pilsner wort was collected in a 10-L carboy and stored at −4° C. until needed. Wort was used as media for propagation of yeasts and used in subsequent fermentations. To produce high gravity wort, Pilsner wort was supplemented with maltose prior to autoclaving. All wort was autoclaved prior to analysis to maintain an aseptic environment.

To create the Pilsner wort, milled 2-row superior Pilsen malt and 2-row premium pale malt (Canada Malting, Calgary, Canada) were added to 1.6 hL of filtered water at 52° C. containing 50 g of $CaSO_4$. The grain and water mixture was manually stirred and held at 50° C. for 30 min. The temperature was raised to 65° C. over the next 30 min while stirring continuously, held at 65° C. for 15 min, raised to 72°

C. while stirring, covered and held at 72° C. for 10 minutes, and then mashed out at 76° C. The wort was then vorlaufed to remove any solids and drained to the boil kettle. Sparge water (1 hL at 80° C.) was sprayed into the mash tun and allowed to completely run off. The original gravity (OG) of the wort was adjusted to 1.046 g/cm$^3$ and the wort was boiled for 90 min.

To create the Lambic wort, milled 2-row pale malt, caramel malt, and wheat malt (Canada Malting, Calgary, Canada) were added to 1.6 hL of filtered water at 54° C. with 120 g of CaSO$_4$. After a 20 minute protein rest, the temperature was raised to 72° C. over the next 45 minutes, and then held at 72° C. for 10 minutes. The temperature was raised to 76° C. and maintained for 10 minutes, and then mashed out at 76° C. The wort was vorlaufed and 1.5 hL of 80° C. sparge water was added. The boil was 90 minutes and the OG was adjusted to 1.057 g/cm$^3$.

1.3. Propagation and Fermentation

To propagate yeast cultures, t-streaks were performed on YPDA using the master glycerol stocks and stored at 30° C. for 48 hours. To create a yeast slurry, two 25-mL flasks (Pyrex, NY, U.S.A.) containing 10 mL of autoclaved wort were inoculated with 1 CFU each and agitated in a shake incubator (New Brunswick Scientific-I26, NJ, U.S.A.) at 22° C. for 48 hours. The two 10-mL portions of yeast slurry were then added to a single portion of 300 mL autoclaved wort in a 1-L baffled flask (Pyrex, NY, U.S.A.) and agitated at 22° C. for 48 hours. Yeast slurry was then pitched to autoclaved wort to create a total of 500 mL volume in a 2-L flask (Pyrex, NY, U.S.A.) with yeast at starting concentration of $2 \times 10^7$ cfu/mL. The samples were capped and then fermented at ale temperature (18 or 22° C.). During fermentation samples were taken daily in order to monitor pH, gravity, cell counts, sugar utilization and alcohol production. After the samples reached a gravity reading of approximately 1.015 g/cm$^3$, they were matured for 3 weeks at 14° C. and sampled weekly for flavor compound analysis. Samples were collected aseptically using a 15-mL serological pipette and stored in 15-mL Falcon tubes (Corning Inc., NY, U.S.A.). Samples were stored at −18° C.

2. Beer Sample Analysis 2.1 Ultra Performance Liquid Chromatography (UPLC®): Amino Acids To characterize the profile of amino acids available to yeasts during fermentation, a reverse phase UPLC® method was employed. The Acquity UPLC including the sample manager, column manager, and photodiode array (PDA) detector was coupled with Empower software for instrument control and data analysis (Waters Corporation, MA, U.S.A.). Separation occurred through an ACCQ-TAG Ultra C18 1.7 μm 2.1×100 mm column with ACCQ-TAG Eluent A and B as mobile phases (Waters Corporation, MA, U.S.A.). The flow rate was 0.7 mL/min with UV absorbance detection at 260 nm.

Samples were degassed in 15-mL conical tubes in the Digital Ultrasonic Cleaner (Fisher Scientific, GA, U.S.A) for 10 min and centrifuged in the Sorvall Legend RT+ (Thermo Scientific™, MA, U.S.A.) for 5 min at 1000×g. Samples were derivatized using the AccQ Tag™ Ultra Reagents (Waters Corporation, MA, U.S.A.). Samples were first diluted 1:3 with deionized H$_2$O and vortexed in 0.5-mL Eppendorf tubes (Fisher Scientific, GA, U.S.A). In 12×32 mm glass total recovery screw vials with LectraBond™ caps (Waters Corporation, MA, U.S.A.), 70 μL of borate buffer (pH 8.0), 10 μL of diluted sample and 20 μL of derivatization reagent were added and thoroughly mixed with a pipette tip after each addition. The samples were capped, vortexed, and heated at 55° C. in the Multi-Blok Barnstead Lab-Line Heater (Thermo Scientific™, MA, U.S.A.) for 10 min. The vials were then cooled to ambient temperature and lightly agitated by hand to remove any air bubbles prior to analysis.

Standards were prepared the day of analysis and derivatized using the same method as used for the samples. L-Amino acid analytical standards (Sigma Aldrich, MO, U.S.A.) were removed from −20° C. freezer storage and combined with borate buffer to create a 50 pmol/μL standard. Borate buffer was used as the diluent to create six standards, ranging from 0.78 to 50 pmol/μL.

High Performance Liquid Chromatography (HPLC): Sugars and Alcohols

HPLC was employed using an anion exchange method to analyze maltose, fructose, glucose, glycerol, ethanol and lactic acid. A Prominence UFLC system (Shimadzu, Kyoto, Japan) was used and included the DGU-20A$_3$ degasser, LC-20AD pumps, SIL-20AC HT autosampler, CBM-20A communications bus model, CTO-20A column oven, RID-10A refractive index (RI) detector and Labsolutions Software for control and analysis.

The autosampler was kept at 4° C. with an injection volume of 10 μL. The column was a 300×7.8 mm Rezex RHM-Monosaccharide H+(Phenomenex, CA, U.S.A.) stored in the column oven at 60° C. The mobile phase was 100% DI Milli-Q (Millipore, MA, U.S.A) water flowing at 0.6 mL/min, degassed and filtered. The RI detector was kept at 40° C. with positive polarity.

Samples were degassed and centrifuged, as described in Section 2.1. Supernatant was collected and 150 μL was pipetted into 1.5-mL clear glass screw thread vials with PTFE/Silicon caps for analysis (Thermo Scientific™, MA, U.S.A.).

USP grade maltose, glucose, fructose, glycerol (Sigma Aldrich, MO, U.S.A.), and denatured anhydrous ethanol (Fisher Scientific, GA, U.S.A) were used to prepare standards. Standards were created by making 30 g/L (w/v) stocks in 10-mL graduated cylinders (Fisher Scientific, GA, U.S.A) and homogenized by stirring. Stocks were then filtered with a 10-mL Luer-Lok™ syringe (BD, NJ, U.S.A.) and 0.45-μm syringe filter (Millipore, MA, U.S.A) to 15-mL Falcon tubes (Corning Inc., NY, U.S.A.) and stored at 4° C. until needed for further use.

2.3 Cellometer: Cell Counts

Cell counts were obtained each day using the Cellometer® Vision (Nexcelom Bioscience, MA, U.S.A.) and included methylene blue, which stains dead eukaryotes blue while "live" cells remain colorless, allowing yeast viability to be determined. Yeasts were diluted 1:10 by mixing 10 μL of yeast sampled, 10 μL 0.1% methylene blue, and 80 μL of DI water. After thorough mixing, 15 μL of diluted sample was pipetted on to the cellometer slide and inserted to the system to perform the cell count; readings were done in triplicate and averaged for each sample.

2.4. Density Meter: Gravity Readings

Throughout fermentation the gravity of the wort was recorded using a density meter, DMA 4500M (Anton-Paar, Graz, A.U.T.). Sample was collected in a 5-mL Injekt™ syringe (B. Braun, Melsungen, D.E.U.), degassed by manual agitation, and inserted into the density meter until the U-tube was visibly filled and no air bubbles remained. Once the temperature reaches 20° C., the U-tube shakes and the resulting oscillation of the liquid is determined. The gravity (g/cm$^3$) and sugar concentration (g/L) were recorded and used to determine when sugar utilization had ended and fermentation was complete.

2.5. pH Meter: Acid Production

The pH of the beer samples was monitored during fermentation using a SevenGo Duo pH Meter and InLab® 413 SG electrode (Mettler Toledo, Greifensee, C.H.E.). The pH meter was calibrated with buffer solutions of pH 4.0, 7.0, and 10.0 (Fisher Scientific, GA, U.S.A) prior to analysis.

2.6. Gas Chromatography-Mass Spectrometry (GC-MS): Aromatic Compounds

GC-MS coupled with head space solid-phase micro extraction (HS-SPME) was used to analyze the aromatic flavor compounds in beer samples throughout maturation. The GC-MS QP2010 SE (Shimadzu, Kyoto, Japan) was paired with GCMS LabSolutions software. A Stabilwax® 30 m×0.32 mm ID×0.25 µm column (Restek, PA, U.S.A.) was stored in the column oven and held at 40° C. for 2 min, then raised to 150° C. at a rate of 3° C./min (38.67 min total run time). Ultra-high purity helium was used as the mobile phase with the flow control mode set to "Linear Velocity", a total flow of 16.6 mL/min, and a column flow of 1.51 mL/min. The injector port was equipped with a low-volume liner for SPME (SGE, Melbourne, A.U.S.) and gas tight septum Thennogreen® LB-2 Septa (Sigma Aldrich, MO, U.S.A.) The injector port was held at 200° C. and operated in splitless mode. The mass spectrometer operated with the ion source temperature and interface temperature held at 200° C. and with 10000 scan speed.

Samples were degassed in 50-mL Falcon tubes (Corning Inc., NY, U.S.A.) in the Digital Ultrasonic Cleaner (Fisher Scientific, GA, U.S.A) for 20 min. Then, 2.7 g of sodium chloride (Fisher Scientific, GA, U.S.A) and an 8-mm stir bar (Fisher Scientific, GA, U.S.A) were added to a clear 15-mL vial with 22-mm hole caps and 22-mm PTFE/silicone septa (Sigma Aldrich, MO, U.S.A.). Then 9.99 mL of degassed beer along with 10 µL of 2-heptanol solution was added to the vials. The 2-heptanol was added as an internal standard, and all vials contained a final concentration of 0.1 mg/L of 2-heptanol.

Samples were vortexed until all salt was in solution, then placed on a Cimarec Stirring Hot Plate (Thermo Scientific™, MA, U.S.A.) inside a 22-mm heating block insert to maintain a temperature of 50° C. The temperature was monitored with an Ertco™ Exact-Temp™ mercury thermometer (Fisher Scientific, GA, U.S.A). After incubating for 5 minutes, a 50/20 µm DVB/CAR/PDMS, Stableflex SPME fiber in a manual SPME holder (Sigma Aldrich, MO, U.S.A.) was inserted into the septum of the sample vial, the fiber was exposed to the headspace, and incubated for 30 min.

The mass spectrometer utilized electron ionization (EI), a quadrupole mass analyzer and the detector was operated in scan mode for analysis. In addition to the chromatographic data obtained, mass spectra data was available for each eluting compound. For unknown compounds detected, a tentative identification was determined by comparing the resulting mass spectra fragmentation pattern with the mass spectra library available with the GCMSsolution Workstation Software. The following analytical grade standards were obtained and injected to confirm compound identity: isobutyl alcohol, isoamyl alcohol, ethyl acetate, phenylethyl acetate, phenyl acetate, isoamyl acetate, isobutyl acetate, ethyl hexanoate, diacetyl, and acetylacetone (Sigma Aldrich, MO, U.S.A.).

Additionally, samples from Phase 2 were sent for external quantitative volatile analysis for comparison of *L. thermotolerans* BB202 to the type strain NRRL Y-8284. This external laboratory conducted volatile analysis according to the standard method Beer-29: Lower boiling volatiles in beer or ale (ASBC). This method utilizes a flame-ionization detector (GC-FID), coupled with a 15 ft×⅛ in stainless steel packed column with 20% Carbowax 20 M on Chromosorb W (HDMS), 60/80 mesh held at 80° C. Helium (30 mL/min) was the mobile phase, with an injector temperature of 170° C. and a detector temperature of 180° C. Sample was introduced to the system via direct injection of 10 µL with an internal standard, and quantitation was accomplished with an external calibration curve using the internal standard.

3. Results 3.1. Preliminary Fermentation Data of *L. thermotolerans* BB202 (strain BB202) (Phase 1)

In Phase 1, *Lachancea thermotolerans* BB202 was fermented at 18° C. in wort to determine whether it could be used as a brewing strain. As shown in Table 5, *L. thermotolerans* BB202 utilized 97.3% of the maltose by Day 6, only reducing a further 1.7 g/L between Day 6 and Day 10 (94.5% total maltose utilized). Similarly, 97.0% of the ethanol was produced by Day 6, with an addition of only 1.2 g/L of ethanol produced between Day 6 and Day 10.

TABLE 5

Preliminary data of *L. thermotolerans* BB202 fermentations at 18° C. in wort (n = 2).

| Day | Maltose (g/L) | Glucose (g/L) | Fructose (g/L) | Glycerol (g/L) | Ethanol (g/L) | ABV % |
|---|---|---|---|---|---|---|
| 1 | 66.8 | 5.1 | 6.7 | 1.4 | 5.9 | 0.8% |
| 2 | 51.0 | 0.1 | 1.0 | 2.0 | 18.6 | 2.4% |
| 3 | 33.2 | 0.1 | 0.9 | 2.3 | 27.2 | 3.5% |
| 4 | 17.6 | 0.3 | 1.3 | 2.8 | 34.3 | 4.4% |
| 5 | 9.3 | 0.2 | 1.2 | 2.9 | 38.4 | 4.9% |
| 6 | 5.4 | 0.5 | 1.4 | 3.0 | 40.2 | 5.1% |
| 7 | 4.6 | 0.5 | 1.4 | 3.1 | 40.5 | 5.1% |
| 8 | 3.9 | 0.5 | 1.3 | 3.2 | 41.4 | 5.3% |
| 9 | 3.7 | 0.5 | 1.3 | 3.2 | 41.5 | 5.3% |
| 10 | 3.7 | 0.5 | 1.3 | 3.2 | 41.4 | 5.3% |

3.2. Fermentation Performance of *L. thermotolerans* BB202 Compared to the Type Strain in Pilsner Wort (Phase 2)

Figure 5:
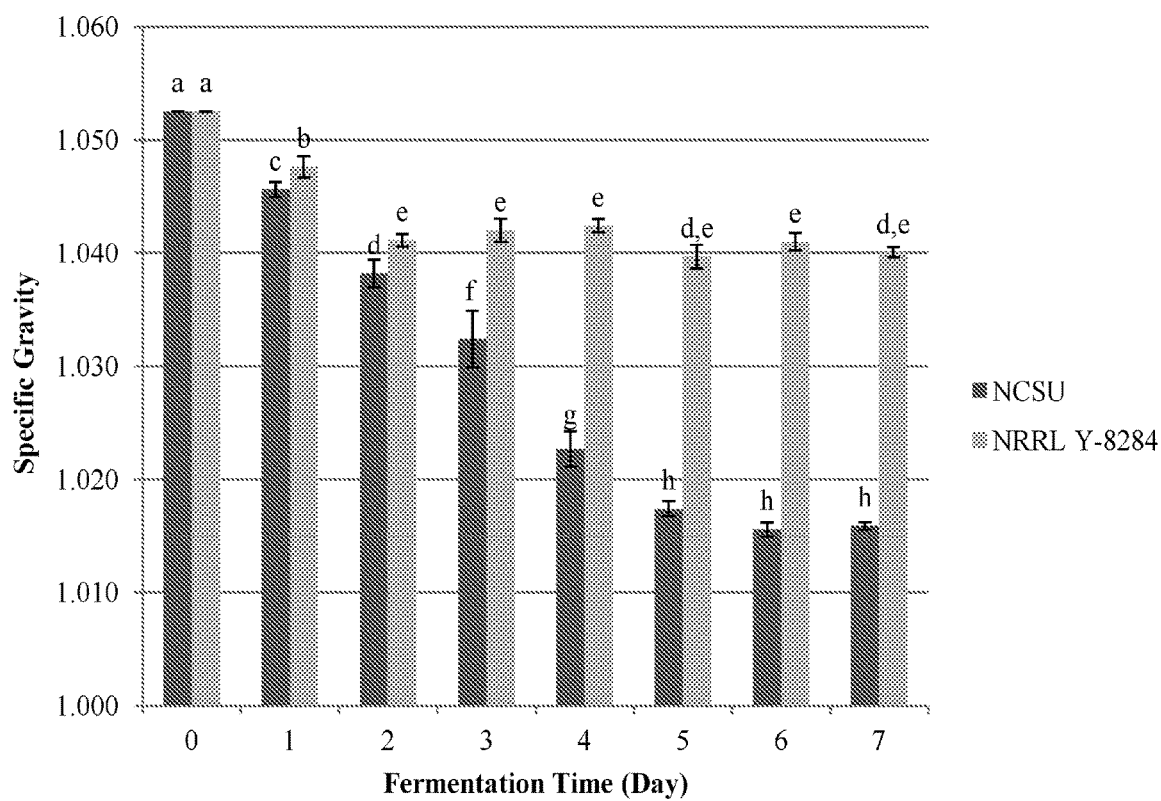
FIG. 5 shows the change in specific gravity of wort by L. thermotolerans strains BB202 (NCSU) (deposited as NRRL Y-67253) and NRRL Y-8284 during fermentation at 18° C. (n=3 with ±1 standard deviation, p<0.05).

In Phase 2, *L. thermotolerans* BB202 was compared to the type strain *L. thermotolerans* NRRL Y-8284 (ATCC® 56472™) in triplicate in laboratory scale fermentations at 18° C. All statistical analysis was conducted using t-tests with p<0.05. Detailed data from these experiments is presented in Table 17 through Table 24. FIG. 5 shows the BB202 strain reduced the specific gravity faster and further than the NRRL Y-8284 strain in wort; the original gravity (OG) was 1.053 (13° P). Sampling of both fermentations was stopped at Day 7 when the gravity of the *L. thermotolerans* BB202 fermentation slowed; the final gravity was 1.016 (45.9 g/L residual sugar). The specific gravity of the *L. thermotolerans* NRRL Y-8284 fermentation slowed after reaching 1.041 on Day 2; the FG was 1.040 (108.9 g/L residual sugar).

Figure 6A:
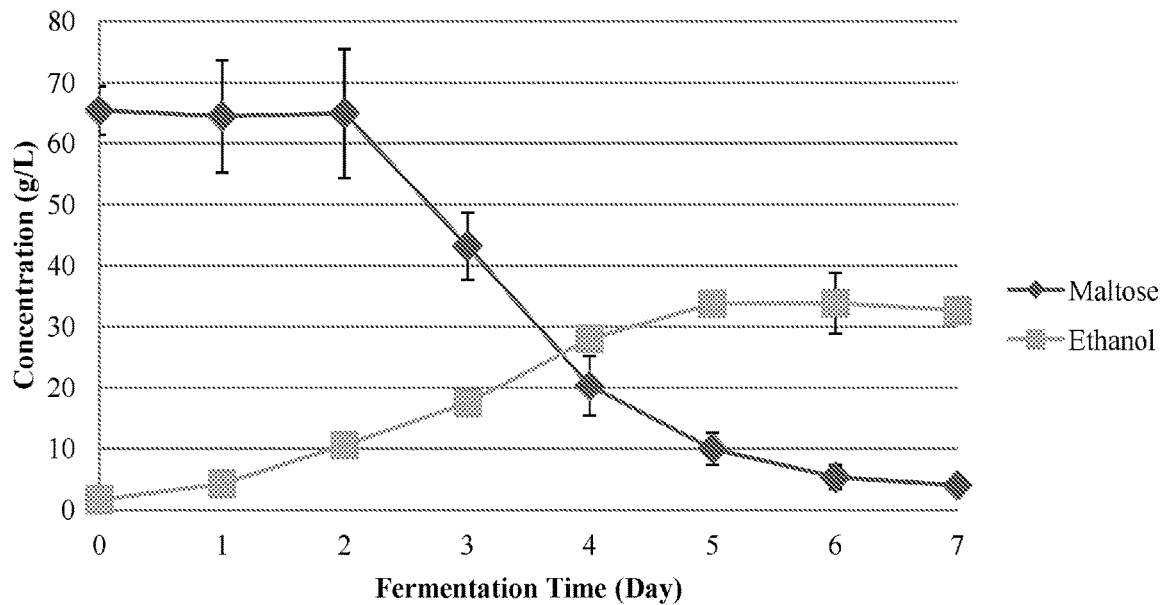
FIG. 6A-6B show the comparison of L. thermotolerans strains BB202 (NCSU) (deposited as NRRL Y-67253) (FIG. 6A) and NRRL Y-8284 (FIG. 6B) maltose utilization and ethanol production at 18° C. (n=3 with ±1 standard deviation).
Figure 6B:
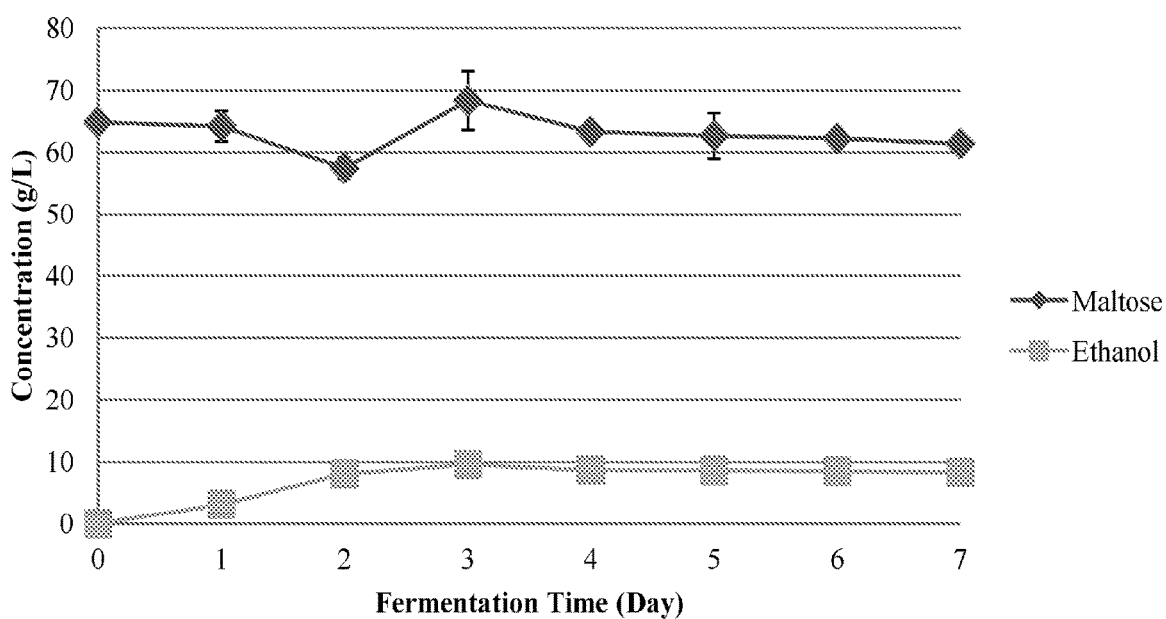

*L. thermotolerans* NRRL Y-8284 did not utilize maltose or produce ethanol as efficiently as *L. thermotolerans* BB202, as displayed in FIG. 6A-6B. *L. thermotolerans* NRRL Y-8284 started at 64.9 g/L maltose and ended at 61.4 g/L (5.4% total maltose utilized). *L. thermotolerans* BB202 started at 65.4 g/L maltose and ended at 4.0 g/L (93.8% total maltose utilized). More ethanol was produced by *L. thermotolerans* BB202, which had a final ABV of 4.15% (32.7 g/L of ethanol). *L. thermotolerans* NRRL Y-8284 did not produce any additional ethanol from Day 2 to Day 7 and had a final ABV of 1.06% (8.4 g/L of ethanol).

Figure 7A:
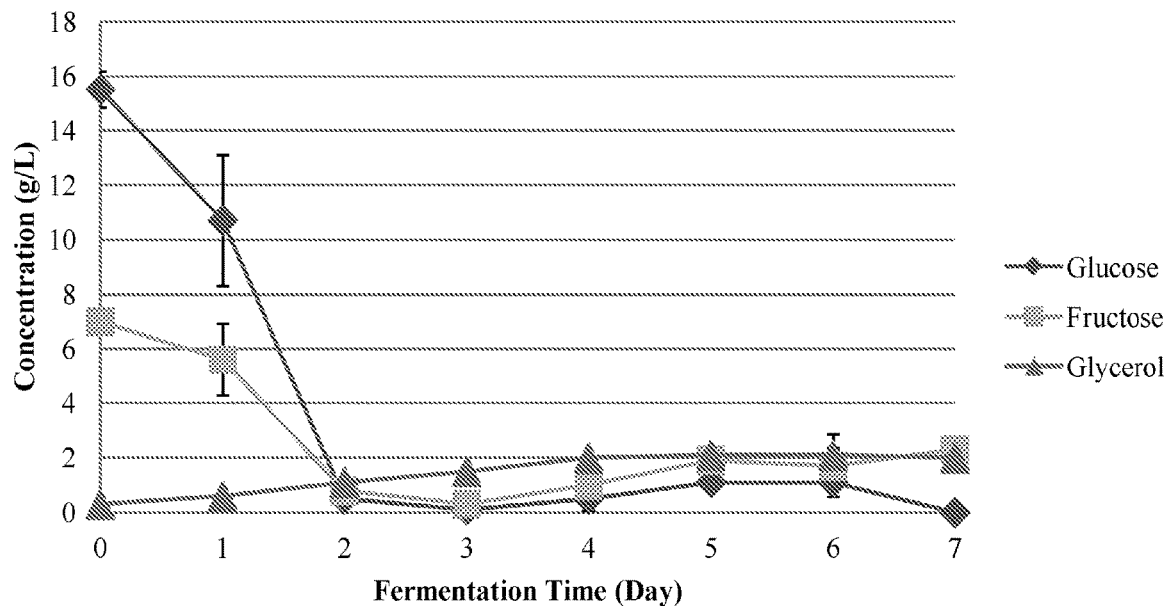
FIG. 7A-7B show the comparison of L. thermotolerans strains BB202 (NCSU) (deposited as NRRL Y-67253) (FIG. 7A) and NRRL Y-8284 (FIG. 7B) sugar utilization and glycerol production at 18° C. (n=3 with ±1 standard deviation).
Figure 7B:
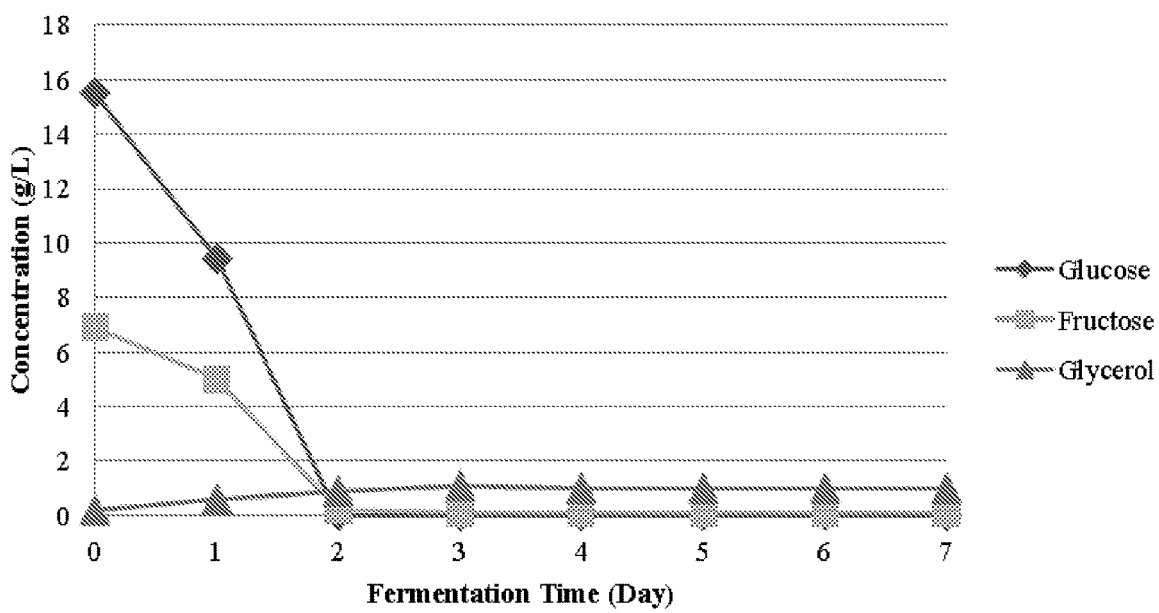

Both *L. thermotolerans* NRRL Y-8284 and BB202 utilized the available glucose and fructose. As seen in FIG. 7A-7B, *L. thermotolerans* NRRL Y-8284 reduced both sugars to completeness by approximately Day 2. *L. thermotolerans* BB202 reduced both sugars by Day 3, but on Day 4 both monosaccharides had increased in concentration. Both strains produced glycerol, but the *L. thermotolerans* BB202 produced more glycerol than *L. thermotolerans* NRRL Y-8284; during fermentation, the BB202 strain produced 1.7 g/L of glycerol compared to NRRL Y-8284 strain, which produced 0.8 g/L.

Figure 8:
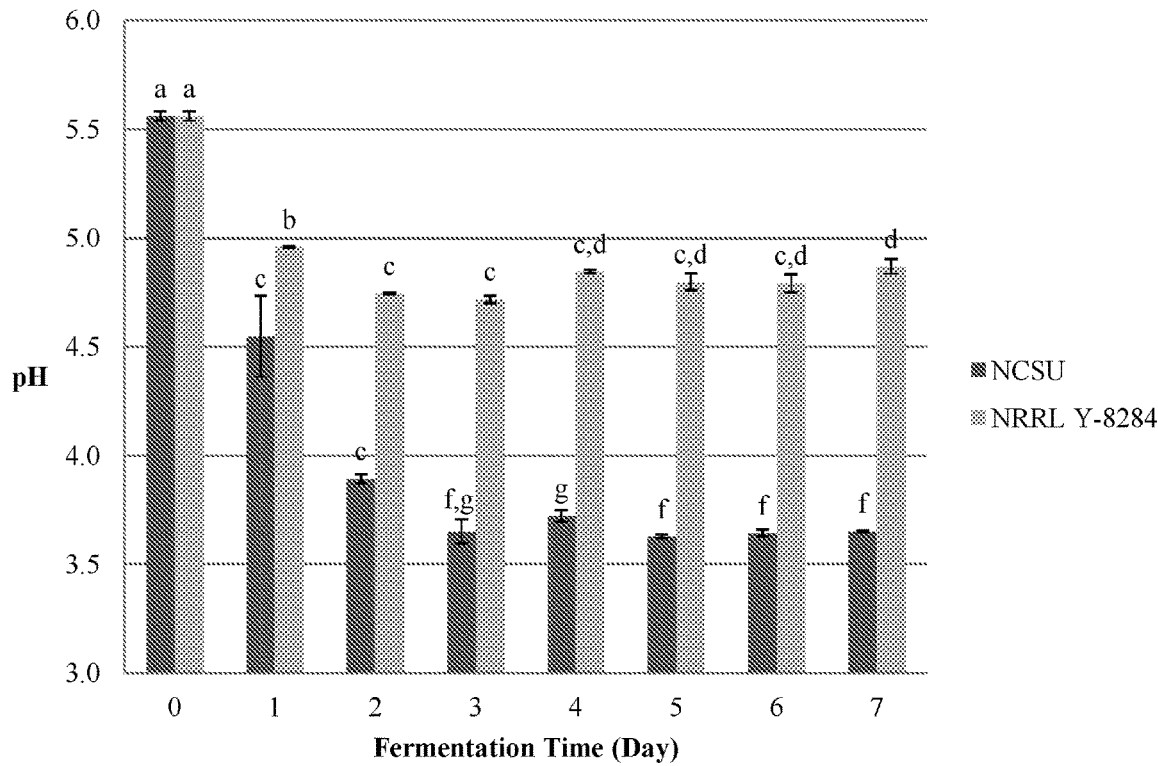
FIG. 8 shows the monitoring of the pH during fermentation of L. thermotolerans BB202 (NCSU) (deposited as NRRL Y-67253) and NRRL Y-8284 at 18° C. (n=3 with ±1 standard deviation, p<0.05).

The pH was monitored during fermentation from an initial wort pH of 5.56 (FIG. 8). *L. thermotolerans* BB202 strain dropped the pH by 1.01 after Day 1 and finished acid production around Day 3 for a final pH of 3.65 (Δ1.91). *L. thermotolerans* NRRL Y-8284 did not produce as much acid as the BB202 strain, dropping the pH by only 0.60 after Day 1 and finishing acid production around Day 2 for a final pH of 4.87 (Δ0.77).

Figure 9:
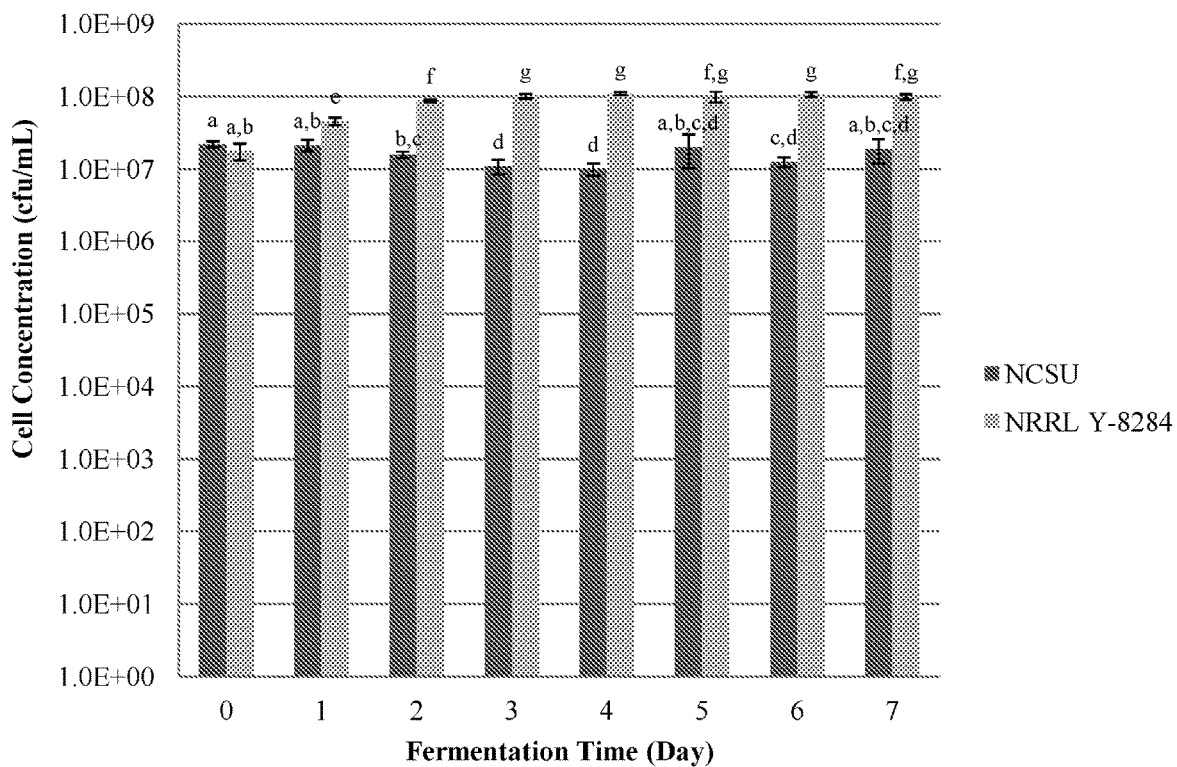
FIG. 9 shows a comparison of cell concentrations of L. thermotolerans BB202 (NCSU) (deposited as NRRL Y-67253) and NRRL Y-8284 during fermentation at 18° C. (n=3 with ±1 standard deviation, p<0.05).

Cell counts were also monitored via a cellometer; *L. thermotolerans* BB202 and NRRL Y-8284 strains were inoculated at 1×10$^7$ cfu/mL and remained viable throughout fermentation, though the type strain did have a higher average concentration and reached concentrations up to 1×10$^8$ cfu/mL during fermentation (FIG. 9).

Amino acids were analyzed at the beginning (Day 0) and end (Day 7) of fermentations for both *L. thermotolerans* BB202 and NRRL Y-8284 strains; note that wort contains 19 amino acids, as it excludes cysteine. Ammonia (NH$_3$) utilization was analyzed for comparison to the type strain. Amino acid utilization is displayed in four groups: Group A (Thr, Ser, Asn, Met, Lys), Group B (Gln, Leu, Ile, Asp, His, Arg, Val, Phe), Group C (Glu, Tyr, Gly, Ala, Trp), and Group D (Proline) (Table 6). Based on the average remaining amino acids, *L. thermotolerans* BB202 utilized Group A more than *L. thermotolerans* NRRL Y-8284. In Group B, *L. thermotolerans* BB202 appeared to produce glutamine compared to *L. thermotolerans* NRRL Y-8284 which utilized all but 24% of the available glutamine. Strain NRRL Y-8284 utilized Group D further than strain BB202. For both *L. thermotolerans* BB202 and NRRL Y-8284, Group D had the highest percentage of amino acids remaining, followed by Group C, Group B, and finally Group A.

TABLE 6

Starting concentration of amino acids and percentage remaining after fermentation of *L. thermotoerans* BB202 and NRRL Y-8284 (n = 3).

| | BB202 | | | NRRL Y-8284 | | |
|---|---|---|---|---|---|---|
| Amino Acid | Starting Conc. (mg/L) | Remaining (%) | Group Average Remaining (%) | Starting Conc. (mg/L) | Remaining (%) | Group Average Remaining (%) |
| GROUP A | | | | | | |
| Thr | 80.2 | 22% | 29% | 89.8 | 10% | 34% |
| Ser | 102.9 | 30% | | 114.6 | 44% | |
| Asn | 129.4 | 34% | | 148.8 | 28% | |
| Met | 48.5 | 30% | | 47.3 | 48% | |
| Lys | 109.5 | 27% | | 121.1 | 41% | |
| GROUP B | | | | | | |
| Gln | 10.4 | 233% | 69% | 12.2 | 24% | 51% |
| Leu | 198.2 | 29% | | 221.5 | 44% | |
| Ile | 80.2 | 35% | | 102.0 | 57% | |
| Asp | 92.5 | 48% | | 99.5 | 43% | |
| His | 60.2 | 63% | | 67.0 | 66% | |
| Arg | 131.7 | 9% | | 153.5 | 36% | |
| Val | 124.9 | 82% | | 167.5 | 79% | |
| Phe | 130.5 | 50% | | 175.9 | 59% | |
| GROUP C | | | | | | |
| Glu | 104.0 | 69% | 78% | 113.0 | 69% | 81% |
| NH3 | 75.1 | 82% | | 81.8 | 94% | |
| Tyr | 147.2 | 84% | | 163.6 | 81% | |
| Gly | 52.0 | 76% | | 59.0 | 76% | |
| Ala | 163.3 | 69% | | 180.3 | 93% | |
| Trp | 46.7 | 86% | | 61.4 | 73% | |
| GROUP D | | | | | | |
| Pro | 498.4 | 98% | 98% | 560.7 | 90% | 90% |

Aromatic analysis was conducted at the beginning of maturation (Week 0) to compare *L. thermotolerans* strain BB202 to strain NRRL Y-8284 (Table 7). These 14 compounds were selected for comparison based upon their high frequency of occurrence among samples analyzed. Aromatics were also identified by their mass spectra. There compounds were analyzed and compared to the internal standard (0.1 mg/L of 2-heptanol) and reported as peak ratio (PR), or the peak area of the analyte divided by the peak area of the internal standard. The 14 compounds included alcohols (5), esters (7), aldehydes (1), and terpenes (1). Of the 14 compounds detected, *L. thermotolerans* BB202 had a higher peak ratio for 13 compounds when compared to NRLL Y-8284. *L. thermotolerans* NRRL Y-8284 had a higher ratio of 1-hexanol detected.

TABLE 7

Aromatic analysis of *L. thermotolerans* BB202 compared to the type strain at the beginning of maturation (Week 0) at 18° C. (n = 3 with one standard deviation reported).

| | | BB202 (Peak Ratio) | | | NRRL Y-8284 (Peak Ratio) | | |
|---|---|---|---|---|---|---|---|
| Elution # | Compound | Average | Standard Deviation | CV (%) | Average | Standard Deviation | CV (%) |
| 1 | Acetaldehyde | 0.21 | 0.02 | 0.12 | 0.06 | 0.01 | 0.11 |
| 2 | Ethyl acetate | 4.16 | 0.81 | 0.19 | 0.46 | 0.12 | 0.27 |
| 3 | Ethyl butyrate | 0.01 | 0.00 | 0.12 | n.d. | n.d. | n.d. |
| 4 | Isobutanol | 0.45 | 0.09 | 0.20 | 0.15 | 0.00 | 0.02 |
| 5 | Isoamyl acetate | 0.35 | 0.02 | 0.06 | 0.07 | 0.02 | 0.32 |
| 6 | Isoamyl alcohol | 9.17 | 1.46 | 0.16 | 3.92 | 0.16 | 0.04 |
| 7 | Ethyl hexanoate | 0.14 | 0.10 | 0.71 | 0.01 | 0.01 | 0.55 |
| 8 | 1-Hexanol | 0.01 | 0.01 | 1.00 | 0.04 | 0.02 | 0.52 |
| 9 | Ethyl octanoate | 0.07 | 0.01 | 0.10 | 0.01 | 0.00 | 0.22 |
| 10 | 2,3-Butanediol | 0.02 | 0.02 | 1.00 | n.d. | n.d. | n.d. |
| 11 | Linalool | 0.12 | 0.02 | 0.19 | 0.08 | 0.01 | 0.12 |
| 12 | Ethyl decanoate | 0.06 | 0.04 | 0.71 | n.d. | n.d. | n.d. |
| 13 | Phenylethyl acetate | 0.01 | 0.00 | 0.17 | n.d. | n.d. | n.d. |
| 14 | Phenylethyl alcohol | 3.09 | 0.06 | 0.02 | 0.99 | 0.09 | 0.09 |

Quantitative volatile analysis was conducted and the results are displayed in Table 8. Of the compounds detected, BB202 produced acetaldehyde in the highest concentration; NRRL Y-8284 produced ethyl acetate in the highest concentration, an order of magnitude more than BB202.

TABLE 8

Quantitative volatile comparison of *L. thermtotolerans* BB202 (n = 3) to NRRL Y-8284 (n = 1).

| Compound | NRRL Y-8284 (ppm) | BB202 (ppm) |
|---|---|---|
| Acetaldehyde | 9.2 | 176.0 |
| Ethyl Acetate | 1018.7 | 21.2 |
| Methanol | 5.6 | 5.8 |
| n-Propanol | 6.0 | 14.7 |
| Isobutanol | 9.2 | 14.1 |
| 1-Butanol | 0.7 | 0.1 |
| Amyl alcohol | 32.6 | 53.8 |

Aromatic analysis was conducted at the beginning (Week 0) and end (Week 3) of maturation for *L. thermotolerans* BB202 (Table 9). Of the 14 compounds analyzed, four increased from Week 0 to Week 3 while the rest decreased the four compounds that increased were acetaldehyde, 1-hexanol, 2,3-butanediol, and ethyl decanoate. The compound with the highest peak ratio at Week 3 is phenylethyl alcohol.

TABLE 9

Aromatic analysis of *L. thermotolerans* BB202 start of maturation (Week 0) and the end of maturation (Week 3) (n = 3 with one standard deviation reported).

| | | Week 0 (Peak Ratio) | | | Week 3 (Peak Ratio) | | |
|---|---|---|---|---|---|---|---|
| Elution # | Compound | Average | Standard Deviation | CV (%) | Average | Standard Deviation | CV (%) |
| 1 | Acetaldehyde | 0.21 | 0.02 | 0.12 | 0.62 | 0.06 | 0.10 |
| 2 | Ethyl acetate | 4.16 | 0.81 | 0.19 | 2.22 | 1.06 | 0.48 |
| 3 | Ethyl butyrate | 0.01 | 0.00 | 0.12 | n.d. | n.d. | n.d. |
| 4 | Isobutanol | 0.45 | 0.09 | 0.20 | 0.36 | 0.09 | 0.24 |
| 5 | Isoamyl acetate | 0.35 | 0.02 | 0.06 | 0.11 | 0.07 | 0.64 |
| 6 | Isoamyl alcohol | 9.17 | 1.46 | 0.16 | 1.75 | 1.48 | 0.84 |
| 7 | Ethyl hexanoate | 0.14 | 0.10 | 0.71 | 0.05 | 0.06 | 1.24 |
| 8 | 1-Hexanol | 0.01 | 0.01 | 1.00 | 0.02 | 0.00 | 0.19 |
| 9 | Ethyl octanoate | 0.07 | 0.01 | 0.10 | 0.05 | 0.01 | 0.12 |
| 10 | 2,3-Butanediol | 0.02 | 0.02 | 1.00 | 0.06 | 0.02 | 0.30 |
| 11 | Linalool | 0.12 | 0.02 | 0.19 | 0.10 | 0.01 | 0.13 |
| 12 | Ethyl decanoate | 0.06 | 0.04 | 0.71 | 0.10 | 0.02 | 0.22 |
| 13 | Phenylethyl acetate | 0.01 | 0.00 | 0.17 | n.d. | n.d. | n.d. |
| 14 | Phenylethyl alc. | 3.09 | 0.06 | 0.02 | 3.08 | 0.55 | 0.18 |

3.3. Fermentation Performance of *L. thermotolerans* BB202 in Regular Pilsner Wort Compared to High-Gravity Pilsner Wort (Phase 3)

Figure 10:
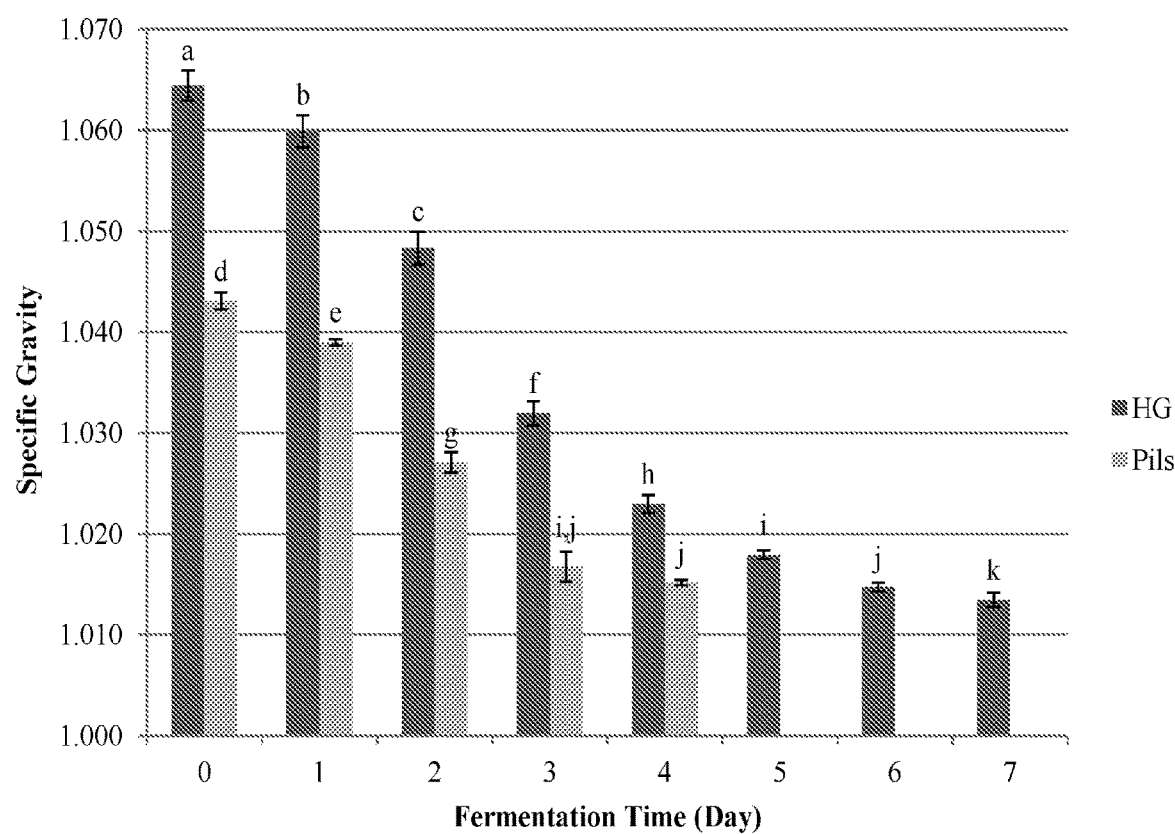
FIG. 10 shows the specific gravity of L. thermotolerans BB202 (NCSU) (deposited as NRRL Y-67253) fermentations in high gravity (HG) and Pilsner (Pils) wort at 22° C. (n=3 with ±1 standard deviation, p<0.05).

In Phase 3, *L. thermotolerans* BB202 was fermented in regular Pilsner (Pils) wort and high gravity Pilsner (HG) wort, or Pilsner wort supplemented with 61.2 g/L maltose; both fermentations were conducted in triplicate. All statistical analysis was conducted using t-tests with $p<0.05$. The detailed data from these experiments, which were used to construct the figures, are contained in Table 25 through Table 32. The single-strain, lab-scale fermentations were conducted at 22° C., with the Pils wort density starting at 1.043 (10.5° Plato) and the HG starting at 1.064 (15.5° Plato). The Pils and HG fermentations lasted four and seven days, respectively, and were stopped when the gravity reached approximately 1.015 (FIG. 10). The final gravity for the regular Pils was 1.015 (43.9 g/L residual sugars) and the HG was 1.013 (39.5 g/L residual sugars).

Figure 11A:
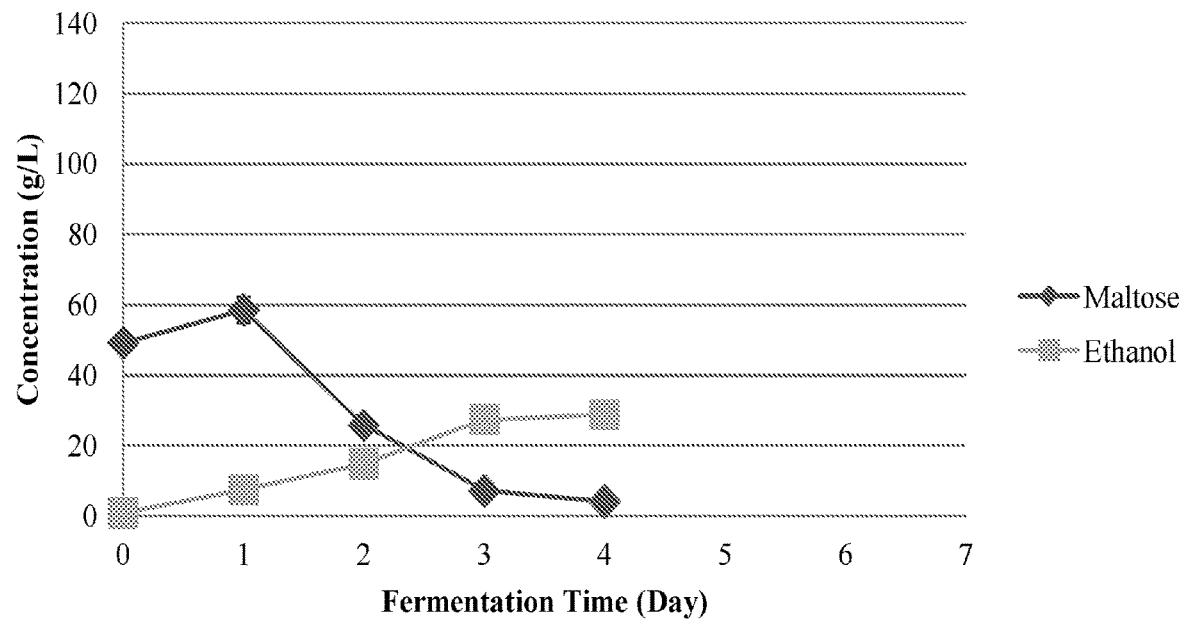
FIG. 11A-11B show a comparison of L. thermotolerans BB202 (NCSU) (deposited as NRRL Y-67253) average maltose utilization and ethanol production at 22° C. in Pilsner (FIG. 11A) and HG (FIG. 11B) wort (n=3 with ±1 standard deviation).
Figure 11B:
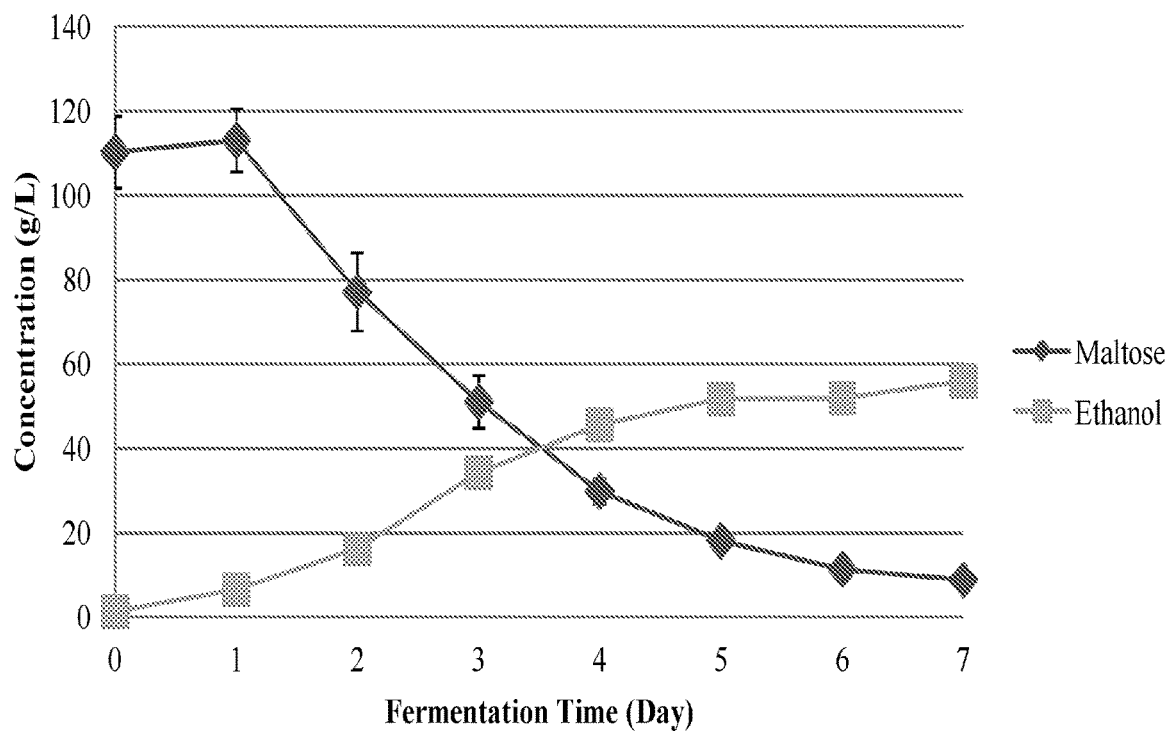

*L. thermotolerans* BB202 was efficient at utilizing the available maltose and producing ethanol in both fermentations (FIG. 11A-11B). In both fermentations, *L. thermotolerans* utilized 92% of the available maltose; the regular Pilsner wort started at 49.2 g/L maltose and the HG wort starting at 110.3 g/L maltose. The HG fermentation generated more ethanol than the regular Pilsner fermentation, yielding 56.0 g/L ethanol (7.10% ABV), versus 28.9 g/L ethanol (3.66% ABV), respectively.

Figure 12A:
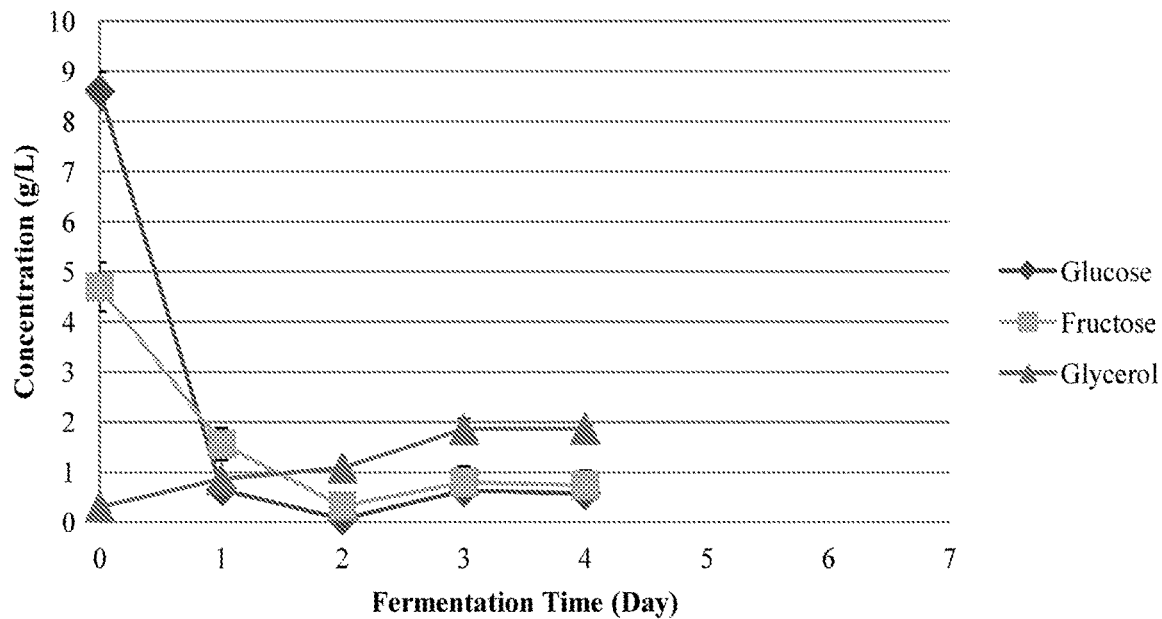
FIG. 12A-12B show a comparison of L. thermotolerans BB202 (NCSU) (deposited as NRRL Y-67253) sugar utilization and glycerol production in Pilsner (FIG. 12A) and HG (FIG. 12B) Pilsner wort at 22° C. (n=3 with +1 standard deviation).
Figure 12B:
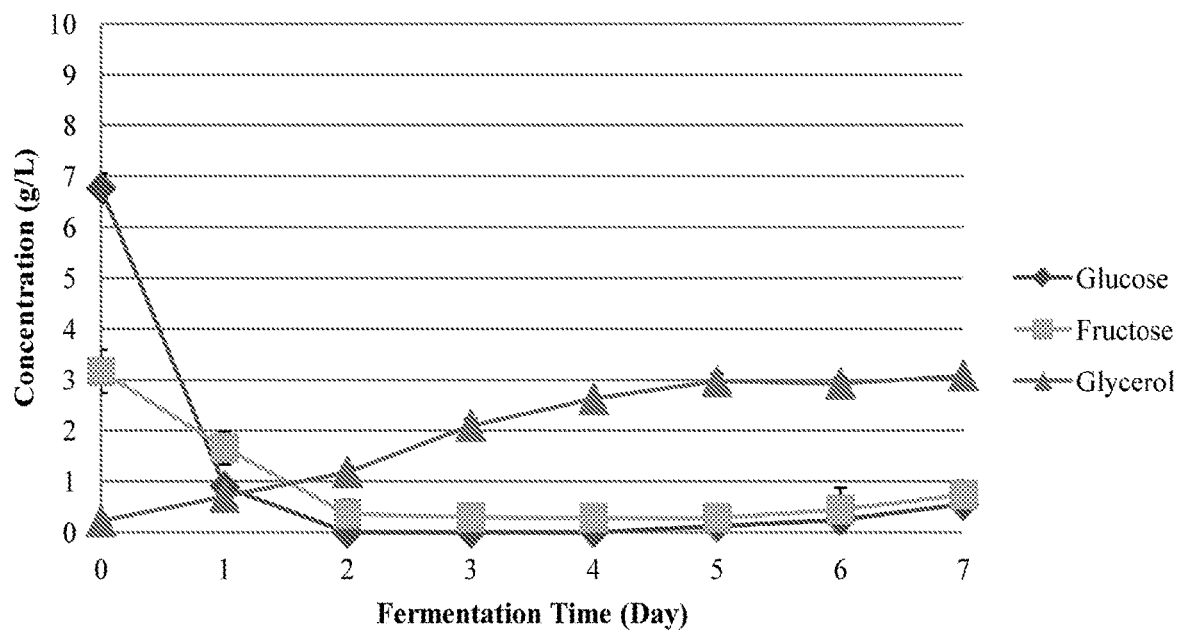

In HG wort, *L. thermotolerans* BB202 utilized glucose and fructose quickly, depleting glucose by Day 2 and reducing the fructose to under 0.5 g/L by Day 3 (FIG. 12A-12B). However, on Day 6 the concentration of both glucose and fructose increased. In the regular Pils wort, BB202 utilized the majority of the available glucose and fructose by Day 2, but monosaccharide concentrations increased on Day 3. Glycerol was produced during fermentation in both HG and regular Pils wort, producing 2.9 g/L and 1.6 g/L of glycerol, respectively.

Figure 13:
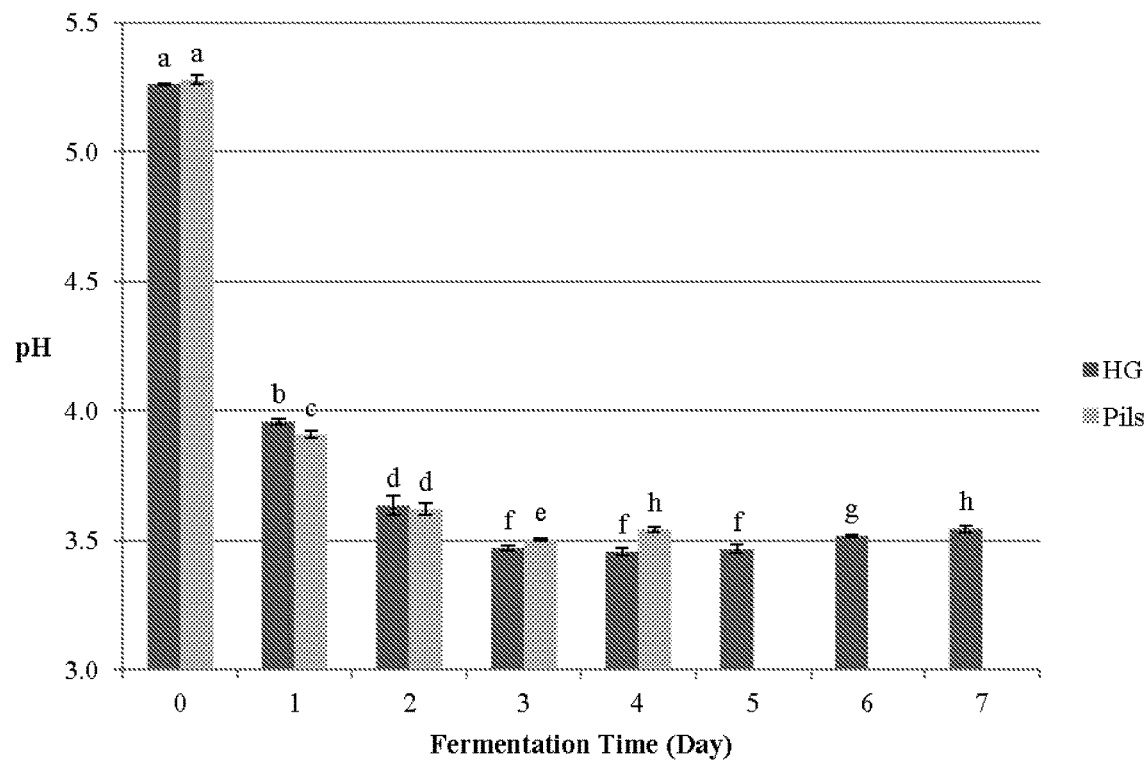
FIG. 13 shows the change in pH by L. thermotolerans BB202 (NCSU) (deposited as NRRL Y-67253) in HG and Pils fermentations at 22° C. (n=3 with ±1 standard deviation, p<0.05).

The pH of both fermentations decreased rapidly, with the regular Pils fermentation starting at 5.28 and HG starting at 5.26 (FIG. 13). The Pils decreased in pH by 1.37 by Day 1, and had a final pH of 3.54 (Δ1.74). The pH of the HG fermentation was reduced by 1.30 by Day 1, and also had a final pH of 3.54 (Δ1.72).

Figure 14:
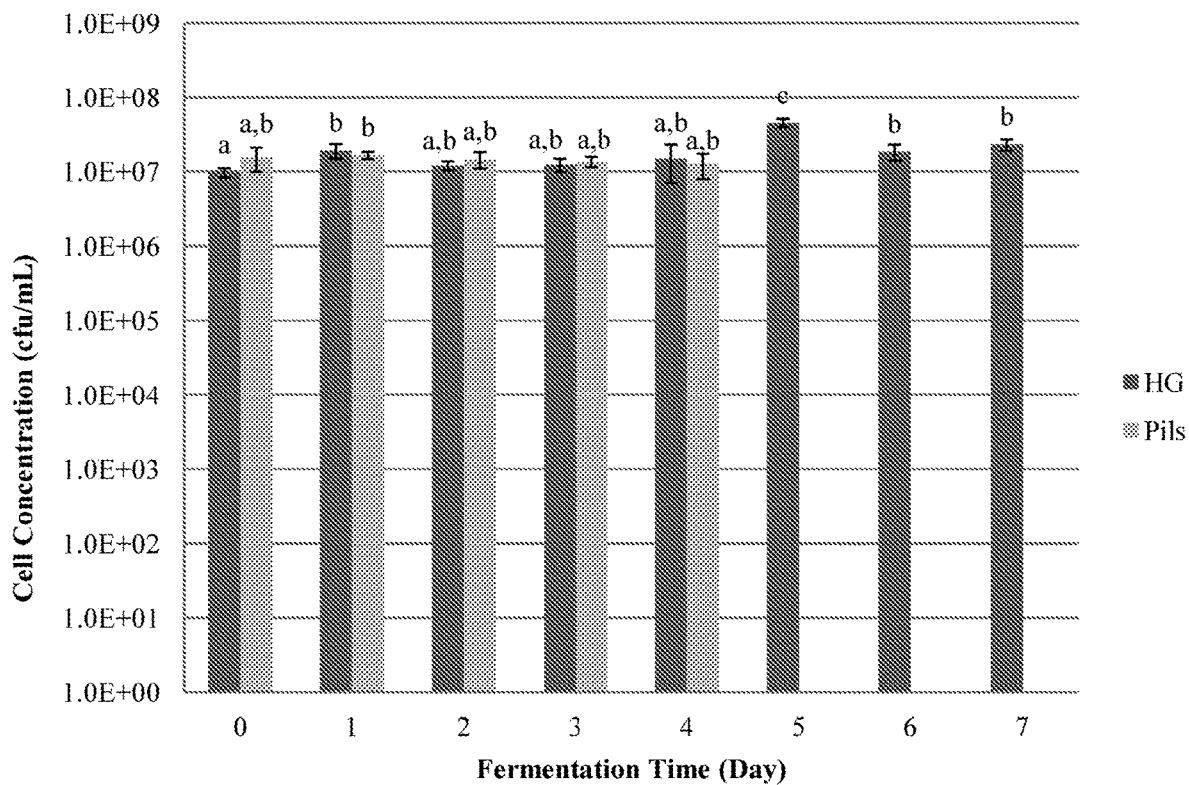
FIG. 14 shows the cell concentration of regular Pils and HG worts during fermentation at 22° C. (n=3 with +1 standard deviation, p<0.05).

Cell counts were also monitored for both fermentations; both high gravity and regular Pils fermentations were inoculated at $1 \times 10^7$ cfu/mL and remained stable and viable throughout fermentation. (FIG. 14).

Amino acids were analyzed at the beginning and end of fermentation and analyses are grouped as reported in Section 3.1. While in the high gravity wort Group D was actually utilized, in the regular wort, the average available amino acid for Group D had increased at Day 4. In the regular fermentation, Group C had two amino acids increase in concentration; tyrosine and tryptophan. In the high gravity fermentation, Group B amino acid, glutamine, had not increased or decreased. In both fermentations (Table 10), Group D had the highest percentage of amino acids remaining, followed by Group C, Group B, and Group A. Additionally, the high gravity fermentation had lower percentage of remaining amino acids for each group compared to the fermentation in regular wort.

TABLE 10

Starting concentration of amino acids and percentage remaining after fermentation of *L. thermotolerans* BB202 in regular and HG Pilsner wort (n = 3).

| Amino Acid | Regular Pilsner Starting Concentration (mg/L) | Remaining (%) | Average Remaining (%) | High Gravity Pilsner Starting Concentration (mg/L) | Remaining (%) | Average Remaining (%) |
|---|---|---|---|---|---|---|
| GROUP A | | | | | | |
| Thr | 70.2 | 18% | 29% | 71.0 | 7% | 9% |
| Ser | 90.3 | 29% | | 102.0 | 11% | |
| Asn | 121.2 | 28% | | 124.0 | 10% | |
| Met | 23.9 | 25% | | 24.0 | 13% | |
| Lys | 89.1 | 0% | | 87.0 | 2% | |
| GROUP B | | | | | | |
| Gln | 25.5 | 77% | 43% | 28.0 | 100% | 26% |
| Leu | 135.0 | 26% | | 171.0 | 3% | |
| Ile | 100.3 | 18% | | 81.0 | 7% | |
| Asp | 77.0 | 45% | | 78.0 | 15% | |
| His | 57.1 | 67% | | 58.0 | 47% | |
| Arg | 123.2 | 8% | | 125.0 | 5% | |
| Val | 131.0 | 65% | | 134.0 | 24% | |
| Phe | 112.6 | 38% | | 142.0 | 4% | |
| GROUP C | | | | | | |
| Glu | 90.1 | 72% | 86% | 91.0 | 36% | 57% |
| Tyr | 133.1 | 108% | | 134.0 | 63% | |
| Gly | 48.0 | 78% | | 49.0 | 71% | |
| Ala | 146.1 | 66% | | 149.0 | 45% | |
| Trp | 39.5 | 106% | | 53.0 | 68% | |
| GROUP D | | | | | | |
| Pro | 449.7 | 104% | 104% | 464.0 | 93% | 93% |

Aromatic analysis was conducted at the beginning (Week 0) of maturation for *L. thermotolerans* BB202 in regular and HG Pilsner wort (Table 11). Of the 14 compounds compared, one remained constant (1-hexanol) and all other compounds were present in higher amounts in the HG Pilsner fermentation.

TABLE 11

Aromatic analysis of *L. thermotolerans* BB202 at the start of maturation in Pils and HG wort (n = 3 with one standard deviation reported).

| | | Pils (Peak Ratio) | | | HG (Peak Ratio) | | |
| --- | --- | --- | --- | --- | --- | --- | --- |
| Elution # | Compound | Average | Standard Deviation | CV (%) | Average | Standard Deviation | CV (%) |
| 1 | Acetaldehyde | 0.09 | 0.02 | 0.21 | 0.24 | 0.03 | 0.14 |
| 2 | Ethyl acetate | 2.09 | 0.34 | 0.16 | 6.17 | 0.62 | 0.10 |
| 3 | Ethyl butyrate | 0.01 | 0.00 | 0.32 | 0.06 | 0.01 | 0.12 |
| 4 | Isobutanol | 0.38 | 0.02 | 0.05 | 1.06 | 0.14 | 0.13 |
| 5 | Isoamyl acetate | 0.27 | 0.06 | 0.22 | 0.70 | 0.04 | 0.06 |
| 6 | Isoamyl alcohol | 7.10 | 1.04 | 0.15 | 16.40 | 1.51 | 0.09 |
| 7 | Ethyl hexanoate | 0.11 | 0.02 | 0.14 | 0.23 | 0.13 | 0.56 |
| 8 | 1-Hexanol | 0.01 | 0.00 | 0.35 | 0.01 | 0.00 | 0.10 |
| 9 | Ethyl octanoate | 0.03 | 0.01 | 0.41 | 0.13 | 0.03 | 0.24 |
| 10 | 2,3-Butanediol | n.d. | n.d. | n.d. | 0.20 | 0.05 | 0.24 |
| 11 | Linalool | 0.02 | 0.00 | 0.06 | 0.03 | 0.01 | 0.16 |
| 12 | Ethyl decanoate | 0.02 | 0.00 | 0.10 | 0.08 | 0.01 | 0.12 |
| 13 | Phenylethyl acetate | 0.27 | 0.15 | 0.55 | 0.43 | 0.20 | 0.46 |
| 14 | Phenylethyl alcohol | 2.41 | 0.33 | 0.14 | 4.41 | 0.28 | 0.06 |

Aromatic analysis was conducted at the end (Week 3) of maturation for *L. thermotolerans* BB202 in Pils arid HG Pilsner wort (Table 12). While at the beginning of maturation, both feimentations had the same peak ratio of 1-hexanol, at the end of maturation, the average peak ratio of 1-hexanol was higher in the HG fermentation. Conversely, linalool had a higher peak ratio in the HG fermentation at the beginning of maturation, while at the end of maturation both fermentations linalool had the same peak ratio. Additionally, at the end of maturation the average peak ratio of phenylethyl acetate was lower in the HG than the Pils wort, even though the HG had a higher peak ratio of phenylethyl acetate than the Pils at the beginning of maturation.

3.4. Fermentation Performance of *L. thermotolerans* BB202 in Lambic Wort at the Pilot Plant Scale (Phase 4)

In Phase 4, at the pilot plant scale (in a 300-L fermenter) *L. thermotolerans* BB202 was tested for the production of a Lambic-style ale; while the Pilsner fermentations were an all barley malt, the Lambic-style recipe includes wheat. The fermentation was conducted at 18° C. The pitching rate of 4 L of active BB202 yeast was halved due to excessive flocculation, for a total of 2 L aerobic active yeast. The gravity was monitored throughout fermentation; the OG was 1.057 (14° P) and fermentation was stopped at Day 25, the FG was 1.011 (33.0 g/L residual sugar). Additional data obtained from this fermentation are contained in Tables 33-34, For the pilot-scale fermentation, maltotriose was analyzed to confirm *L. thermotolerans* BB202 could utilize the second most abundant sugar in wort; these comprise the total sugars reported (Table 13). After Day 25, there was no fructose detectable in the sample and the residual glucose was less

TABLE 12

Aromatic analysis of *L. thermotolerans* BB202 at Week 3 of maturation in Pils and HG wort (n = 3 with one standard deviation reported).

| | | Pils (Peak Ratio) | | | HG (Peak Ratio) | | |
| --- | --- | --- | --- | --- | --- | --- | --- |
| Elution # | Compound | Average | Standard Deviation | CV (%) | Average | Standard Deviation | CV (%) |
| 1 | Acetaldehyde | 0.13 | 0.02 | 0.12 | 0.24 | 0.02 | 0.07 |
| 2 | Ethyl acetate | 0.19 | 0.01 | 0.05 | 3.27 | 0.90 | 0.27 |
| 3 | Ethyl butyrate | n.d. | n.d. | n.d. | 0.11 | 0.08 | 0.69 |
| 4 | Isobutanol | 0.18 | 0.01 | 0.05 | 0.92 | 0.12 | 0.13 |
| 5 | Isoamyl acetate | 0.01 | 0.00 | 0.19 | 0.53 | 0.27 | 0.51 |
| 6 | Isoamyl alcohol | 3.56 | 0.19 | 0.05 | 16.47 | 2.36 | 0.14 |
| 7 | Ethyl hexanoate | 0.01 | 0.00 | 0.36 | 0.39 | 0.15 | 0.38 |
| 8 | 1-Hexanol | 0.01 | 0.00 | 0.13 | 0.02 | 0.01 | 0.35 |
| 9 | Ethyl octanoate | 0.27 | 0.36 | 1.34 | 0.32 | 0.12 | 0.38 |
| 10 | 2,3-Butanediol | 0.01 | 0.00 | 0.31 | 0.11 | 0.03 | 0.28 |
| 11 | Linalool | 0.03 | 0.00 | 0.15 | 0.03 | 0.00 | 0.06 |
| 12 | Ethyl decanoate | n.d. | n.d. | n.d. | 0.01 | 0.01 | 0.90 |
| 13 | Phenylethyl acetate | 0.35 | 0.46 | 1.32 | 0.16 | 0.05 | 0.32 |
| 14 | Phenylethyl alcohol | 1.80 | 0.16 | 0.09 | 4.12 | 0.86 | 0.21 | than 1 g/L. Maltose was the most abundant sugar analyzed and was the most reduced (Δ64.0 g/L). Maltotriose was the second most abundant, and had the second highest quantity utilized (Δ24.4 g/L), but had the lowest percent utilization (84% utilized).

TABLE 13

Sugar utilization of *L. thermotolerans* BB202 in Lambic wort (n = 1).

| Day | Maltotriose (g/L) | Maltose (g/L) | Glucose (g/L) | Fructose (g/L) | Total Sugars (g/L) |
|---|---|---|---|---|---|
| 0 | 29.0 | 67.0 | 18.7 | 6.8 | 121.5 |
| 25 | 4.8 | 3.5 | 0.8 | n.d. | 9.0 |
| % Utilized | 84% | 96% | 97% | 100% | 93% | n.d. = not detected

Table 14 displays the byproducts of the Lambic-style fermentation. In addition to ethanol and glycerol production, propionic, acetic and lactic acid were analyzed. Of these acids, only lactic acid was detected and was found to have reached 7.3 g/L by Day 25. The Lambic-style fermentation also produced 2.4 g/L of glycerol and had a final ABV of 6.84%.

TABLE 14

Production of acid, glycerol and ethanol by *L. thermotolerans* BB202 in Lambic wort (n = 1).

| Day | Lactic Acid (g/L) | Glycerol (g/L) | Ethanol (g/L) | ABV (%) |
|---|---|---|---|---|
| 0 | n.d. | n.d. | n.d. | n.d. |
| 25 | 7.33 | 2.37 | 53.96 | 6.84% | n.d. = not detected

Figure 15:
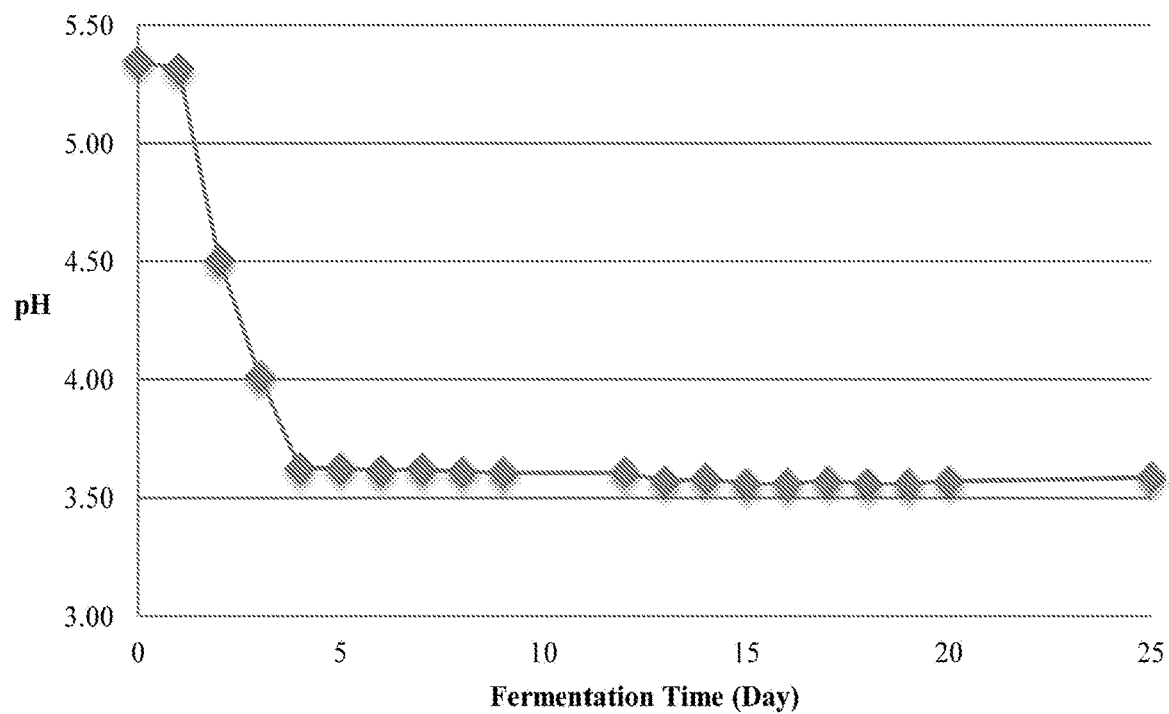
FIG. 15 shows the change in pH during fermentation of L. thermotolerans BB202 (NCSU) (deposited as NRRL Y-67253) in Lambic-style wort (n=1).

The pH was recorded throughout fermentation. The pH started at 5.35 and reached a final pH of 3.60 (Δ1.75). The majority of acid production was completed by Day 4 (FIG. 15) and remained fairly constant until Day 25; the final pH was 3.63.

Amino acids were analyzed at the beginning and end of fermentation and analyses are grouped as reported in Section 3.1. Group A utilized all amino acids to a concentration below 25 g/L. Group B utilized amino acids to concentrations ranging between 25 g/L to 100 g/L. Group C utilized amino acids to concentrations ranging between 40 g/L to 150 g/L. For the Lambic-style fermentation, Group D had the highest average remaining amino acid percentage (106%), followed by Group C (88%), Group B (50%), and Group A (29%), as shown in Table 15. Group D, or proline, increased in concentration. In Group C, glycine also increased in concentration during fermentation.

TABLE 15

Starting concentration of amino acids and percentage remaining after fermentation of *L. thermotolerans* BB202 in Lambic wort (n = 1).

| Amino Acid | Lambic Fermentation | | |
|---|---|---|---|
| | Starting Concentration (mg/L) | Remaining (%) | Group Average Remaining (%) |
| GROUP A | | | |
| Thr | 77.2 | 8% | 29% |
| Ser | 104.7 | 15% | |

TABLE 15-continued

Starting concentration of amino acids and percentage remaining after fermentation of *L. thermotolerans* BB202 in Lambic wort (n = 1).

| Amino Acid | Lambic Fermentation | | |
|---|---|---|---|
| | Starting Concentration (mg/L) | Remaining (%) | Group Average Remaining (%) |
| Asn | 122.8 | 19% | |
| Met | 43.1 | 25% | |
| Lys | 105.5 | 12% | |
| GROUP B | | | |
| Gln | 49.4 | 86% | 50% |
| Leu | 200.3 | 23% | |
| Ile | 90.9 | 33% | |
| Asp | 85.9 | 38% | |
| His | 60.8 | 66% | |
| Arg | 155.9 | 42% | |
| Val | 149.7 | 60% | |
| Phe | 163.1 | 49% | |
| GROUP C | | | |
| Glu | 103.7 | 75% | 88% |
| Tyr | 148.8 | 84% | |
| Gly | 48.2 | 114% | |
| Ala | 160.7 | 96% | |
| Trp | 66.3 | 69% | |
| GROUP D | | | |
| Pro | 581.3 | 106% | 106% |

Figure 16:
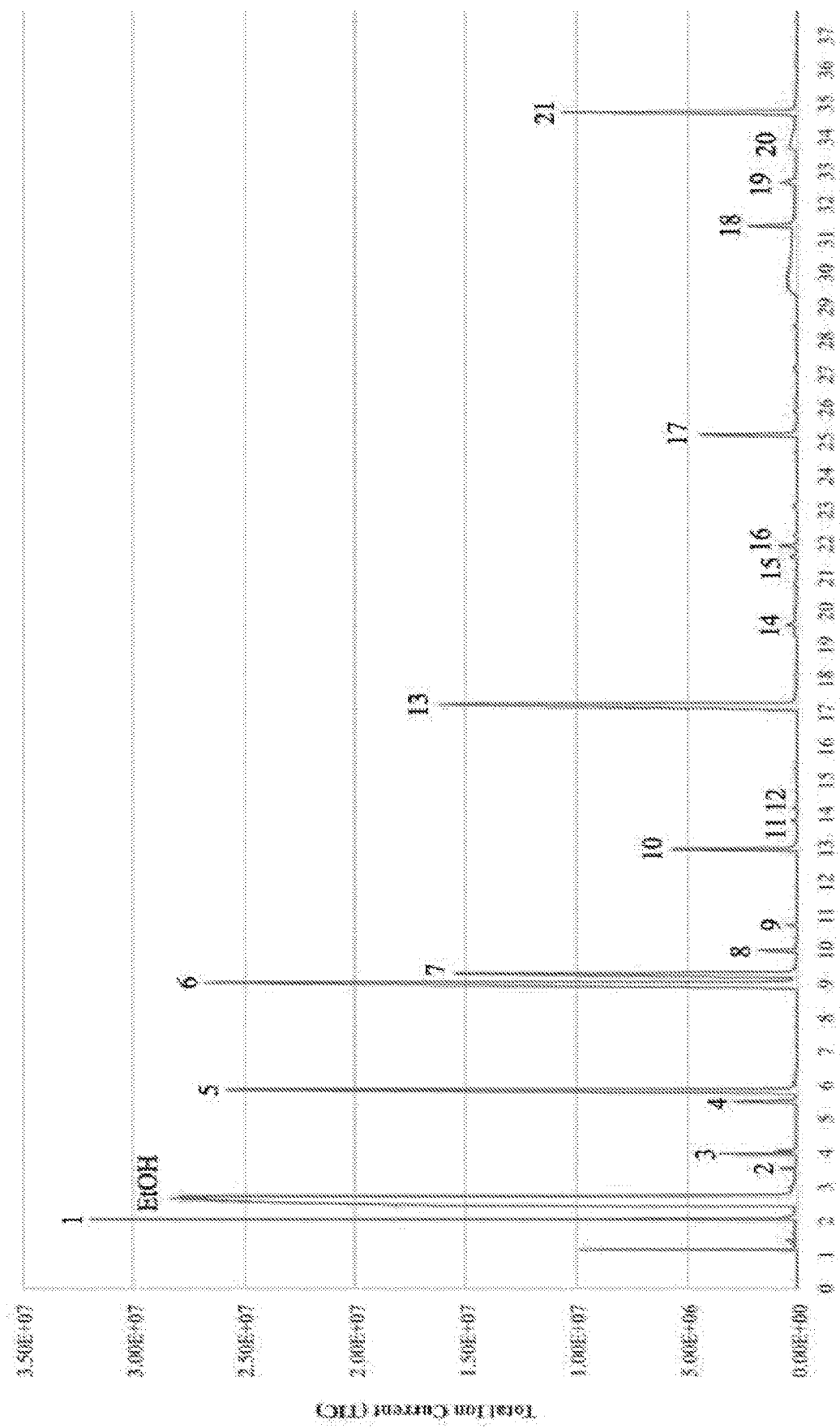
FIG. 16 shows a chromatogram of aromatic analysis of Lambic-style fermentation at pilot-scale; peaks are labeled with a peak number and correspond to Table 8 showing the identified compound, and peak ratio average (n=1).

Aromatic analysis was conducted at the end of maturation for *L. thermotolerans* BB202 in Lambic-style wort; the resulting chromatogram is displayed in FIG. 16. From resulting mass spectra, 19 compounds were tentatively identified; these compounds include 11 esters, 6 alcohols, 1 aldehyde and 1 acid. The five compounds with the highest average peak ratios were isoamyl alcohol, ethyl octanoate, isoamyl acetate, ethyl hexanoate, ethyl acetate, phenylethyl alcohol. Note that acetaldehyde is not detected in the Lambic fermentation.

TABLE 16

Compounds identified from *L. thermotolerans* BB202 in Lambic-style wort via mass spectra.

| Peak # | Compound | Peak Ratio |
|---|---|---|
| 1 | Ethyl acetate | 3.56 |
| 2 | Isoburyl acetate | 0.08 |
| 3 | Ethyl butyrate | 0.41 |
| 4 | Isobutanol | 0.58 |
| 5 | Isoamyl acetate | 6.57 |
| 6 | Isoamyl alcohol | 9.77 |
| 7 | Ethyl hexanoate | 4.28 |
| 8 | Styrene | 0.35 |
| 9 | Acetic acid, hexyl ester | 0.08 |
| 10 | 2-Heptanol | 1.00 |
| 11 | Ethyl lactate | 0.04 |
| 12 | 1-Hexanol | 0.04 |
| 13 | Ethyl octanoate | 6.67 |
| 14 | 2-Ethylhexanol | 0.07 |
| 15 | 2,3-Butanediol | 0.06 |
| 16 | Linalool | 0.15 |
| 17 | Ethyl decanoate | 1.04 |
| 18 | Phenylethyl acetate | 0.47 |
| 19 | Ethyl laurate | 0.17 |
| 20 | Caproic acid | 0.38 |
| 21 | Phenylethyl Alcohol | 2.46 |

6. Discussion

Phase 1. In Phase 1, preliminary data demonstrated that *L. thermotolerans* BB202 could perform the two most important functions required of a brewing strain: the assimilation of the primary sugar, maltose, and production of the primary desired product, ethanol. By Day 4, 74% of the available maltose was utilized and 80% of the total ethanol was produced.

Standard brewing yeasts (i.e., *S. cerevisiae* and *S. pastorianus*) can only assimilate and metabolize glucose, fructose, maltose and maltotriose (sucrose is broken down extracellularly). The sugars are assimilated in a preferential order with glucose and fructose being metabolized first, followed by maltose and maltotriose. Similar results were seen in fermentations with *L. thermotolerans* BB202, which utilized glucose and fructose first, followed by maltose and maltotriose. Results showed that while glucose and fructose were quickly utilized, they increased in concentration starting on Day 4. Brewer's yeasts have invertases that hydrolyze sucrose (to fructose and glucose) outside of the yeast cell, where as the other sugars are able to be transported into the cytoplasm. This suggests that *L. thermotolerans* BB202 also has invertases to hydrolyze sucrose, resulting in the increased concentrations of glucose and fructose over time. The metabolism of glucose, fructose and sucrose is important for brewers yeast as these sugars are readily available in wort.

Glycerol was also produced during fermentation; 1.8 g/L of glycerol was produced and 78% of the glycerol was produced by Day 4. All brewing strains produce glycerol, which is a viscous sugar alcohol that has a slightly sweet taste, and mostly contributes to body in fermented beverages (Scanes, 1998). In beer, glycerol ranges from 1 to 3 g/L and has a taste threshold of 10 g/L. Based on these values, *L. thermotolerans* BB202 produces glycerol within the desirable range. This means glycerol can contribute to the positive mouthfeel of beer made by *L. thermotolerans* BB202 without occurring over the flavor threshold, and disturbing the balance of the beer.

Phase 2. In Phase 2, *L. thermotolerans* BB202 distinguished itself metabolically and proved to be a superior brewing strain when compared to the type strain, *L. thermotolerans* NRRL Y-8284. *L. thermotolerans* BB202 was able to utilize more sugars than *L. thermotolerans* NRRL Y-8284. The NRRL Y-8284 strain demonstrated the ability to utilize glucose and fructose to completion by Day 2; however, these values did not increase like they did in fermentations with the BB202 strain. This suggests that *L. thermotolerans* NRRL Y-8284 does not contain the same invertases, or levels of invertases, that *L. thermotolerans* BB202 does. A major difference between the two yeasts was the assimilation of maltose; by Day 4, *L. thermotolerans* BB202 had utilized 69% of the available maltose, while *L. thermotolerans* NRRL Y-8284 had only reduced the maltose by 2%.

Likely due to this inability to metabolize maltose, *L. thermotolerans* NRRL Y-8284 produced less ethanol and glycerol than *L. thermotolerans* BB202. *L. thermotolerans* NRRL Y-8284 had reached an ABV of 1.02% by Day 2, and did not significantly increase after that time; the glycerol produced totaled 0.8 g/L, which is lower than the average glycerol expected in beer. Conversely, *L. thermotolerans* BB202 produced ethanol throughout fermentation and reached a final ABV of 4.15%; a total of 1.7 g/L of glycerol was produced, which falls in line with the average glycerol range expected.

Cell counts and pH were monitored throughout fermentation and, again, differed between the two *L. thermotolerans* yeast strains. Both strains were pitched at $1 \times 10^7$ cells/mL; while *L. thermotolerans* BB202 remained viable throughout fermentation at $1 \times 10^7$ cells/mL, *L. thermotolerans* NRRL Y-8284 remained viable and actually increased to $1 \times 10^8$ cells/mL during the fermentation. Both strains reduced the pH of the wort, but *L. thermotolerans* BB202 was able to reduce the pH (A 1.91) more than *L. thermotolerans* NRRL Y-8284 (A 0.69). It is likely that *L. thermotolerans* BB202 was able to produce more acid because of its ability to metabolize more of the available wort sugars, and utilize them as a carbon sources to produce more acids.

Differences between the two strains were also observed comparing their utilization of amino acids. When comparing the average percent remaining of the amino acid groups, *L. thermotolerans* BB202 utilized Group A and Group C more than *L. thermotolerans* NRRL Y-8284. However, in the *L. thermotolerans* BB202 fermentation, glutamine (Group B) was produced during fermentation. This data point skews the average percent remaining of Group B for *L. thermotolerans* BB202. However, it is in line with literature on typical brewer's yeast, which has determined *Saccharomyces* can synthesize glutamine from glutamate and ammonia (catalyzed by the glutamine synthase encoded by GLN1) (Pires, 2015). Adjustments could be made in Group B, as arginine was the most utilized amino acid by *L. thermotolerans* BB202, it could be moved to Group A for future analysis.

Aromatic comparisons were conducted at NC State and in an external laboratory for the comparison of *L. thermotolerans* BB202 and NRRL Y-8284. Our data showed strain BB202 had a higher peak ratio for all compounds, except 1-hexanol. According to the ASBC Flavor Database (2014) 1-hexanol has aroma descriptors of "coconut, green leaves and unpleasant". Data from the external laboratory showed that strain NRRL Y-8284 had an extremely high concentration of ethyl acetate (1018.72 ppm) compared to BB202 (21.21 ppm); ethyl acetate has a "solvent, fruity, sweet, estery" aroma and a flavor threshold ranging from 25-45 ppm in beer (ASBC, 2014). It should be noted that results from NC State show that ethyl acetate is higher in *L. thermotolerans* BB202 fermentations; these differences in results may be attributed to the fact that the external laboratory utilized a direct injection method (ASBC, Beer-29), while NC State results were obtained using solid-phase microextraction (SPME) as a sample preparation technique. Further results from the external laboratory showed that strain BB202 was well above the flavor threshold (10-20 ppm) for acetaldehyde (175.96 ppm) and within the threshold range (50-70 ppm) of amyl alcohol (53.75 ppm). All other compounds for BB202 and NRRL Y-8284 were below their flavor thresholds.

For *L. thermotolerans* NSCU, aromatic evaluation was done for Week 0 of maturation (end of fermentation) and Week 3 of maturation. While most compounds either stayed consistent or decreased in peak ratio, acetaldehyde increased from Week 0 (0.21 peak ratio) to Week 3 (0.62). The purpose of maturation is to allow flavors to mellow and produce a more balanced beer (e.g., diacetyl is an off flavor that is reduced by yeasts during maturation). This indicates that *L. thermotolerans* BB202 may not be able to reduce acetaldehyde during maturation, and special care should be taken to reduce the amount of acetaldehyde produced during fermentation. This could be a potential issue, as acetaldehyde has a 'grassy' off-flavor when present above its flavor threshold (Meilgaard, 1975).

Phase 3. In Phase 3, *L. thermotolerans* BB202 was fermented in regular Pilsner (10.5° P) and high gravity Pilsner (15.5° P) worts. Like in previous fermentations with *L. thermotolerans* BB202, levels of glucose and fructose were rapidly depleted and then slightly increased in concentration. *L. thermotolerans* BB202 was able to utilize 92% of the available maltose in both fermentations. Brewers utilize high gravity brewing (typically 16-18° P) to increase their volumetric productivity, saving labor and energy costs (He, 2014); thus, it is desirable for brewing yeasts to be able to utilize a high concentration of sugars for economical reasons. Our data demonstrates *L. thermotolerans* BB202 was able to ferment the increased sugar concentration and can be used for high gravity brewing.

*L. thermotolerans* BB202 was able to produce more ethanol and glycerol in the high gravity wort than the regular wort; this increased production is due to the increased maltose concentration (i.e., carbon source). Again, the glycerol produced fell within the average range of 1 to 3 g/L; the regular fermentation produced 1.55 g/L and high gravity produced 2.86 g/L. With ethanol production, the regular fermentation had a final ABV of 3.66%, while the high gravity fermentation reached 7.10%. The approximate concentration of ethanol in beer is 4.44% ABV (Hutkins, 2006) and ABV typically ranges from 4-6%; however, certain styles may reach as high as 12% ABV.

*Saccharomyces* species are able to produce and tolerate high ethanol concentrations (e.g., some wine fermentations may reach up to 16% ABV). Relative to other non-*Saccharomyces* yeast in wine, *L. thermotolerans* is known to have a moderately high ethanol tolerance of <13.5 v/v % (Moreno-Arribas, 2009). A study of pure culture fermentations in wine found from 163.00 g/L sugars, *L. thermotolerans* TH942 made 7.58 v/v % ethanol compared to *S. cerevisiae* SCM952 9.60 v/v % (Kapsopoulou, 2005).

Our data demonstrated that the BB202 strain can produce sufficient ethanol to cover the typical range of beers; furthermore, the BB202 strain can produce concentrations of ethanol higher than in average beer. It is important that *L. thermotolerans* BB202 be able to produce and withstand a large quantity of ethanol to be comparable to *Saccharomyces* as a brewing yeast. Yet, it is also important for brewers to balance the flavors of a beer, and high concentrations of ethanol can yield a strong, solvent aroma and taste.

Comparing the average percent of amino acids remaining, the high gravity fermentation reduced Groups A, B, C and D further than the regular fermentation. For brewing, the carbon to nitrogen (C:N) ratio is low in all-malt wort fermentations, and after fermentation, when yeast growth has ceased, nitrogenous compounds are abundant (He, 2014). However, by supplementing adjuncts like sugar syrups, the C:N ratio increases and the available nitrogen is diluted (He, 2014). Proline is the least preferred amino acid by yeasts, and is not typically utilized during fermentation. Piddocke et al. (2009) found that with an increase in gravity, some proline was assimilated by *Saccharomyces* under microaerobic conditions. Our results show that *L. thermotolerans* BB202 also began to assimilate proline by the end of fermentation in high gravity wort (proline was not utilized in the regular fermentation). It is important for amino acids to be supplemented with high gravity brewing as a lack of nitrogen affects metabolic processes (i.e., higher alcohol production).

Different sugar adjuncts can affect the flavor of beer. Piddocke et al. (2009) determined that more balanced beer was achieved when the gravity was increased by adding maltose syrup as opposed to glucose syrup; additionally, they determined an increased gravity resulted in an increase in the concentration of ethyl acetate and isoamyl acetate in the final beer. Negative effects associated with high gravity brewing include increased acetate esters and higher alcohol concentrations; Anderson and Kirsop (1974) observed an 8-fold increase in acetate ester production occurred when specific gravity was doubled. Additionally, elevated concentrations of higher alcohols and volatile esters were found in high gravity brewing (16° P) compared to normal gravity (13° P) (He, 2014). Aromatic analysis of *L. thermotolerans* BB202 fermentations displayed increased aromatic production, as 13 of the aromatics observed were found in higher quantities in the high gravity beer. It is important for brewers to manage ester and higher alcohol production, or resulting beers can have overly fruity or solvent-like aromas (He, 2014). However, no true conclusions can be made about the flavor imparted by these detected compounds until their exact concentrations are determined and compared to the flavor thresholds of those compounds in acidic beer.

Phase 4. As previous fermentations demonstrated, *L. thermotolerans* BB202 assimilated glucose, fructose, and maltose. As maltotriose had not been analyzed in previous phases, it was analyzed and confirmed to be assimilated by *L. thermotolerans* BB202 (84% utilized). Again, the glycerol produced fell in the desirable range (2.37 g/L) and the ethanol production exceeded the average range of beer (6.84% ABV).

The pH of wort is approximately 5.6, with the pH of beer being approximately 4.2. Comparatively, beer produced from feimentations with *L. thermotolerans* BB202 is more acidic, and beer from all phases ranged in pH from 3.54-3.65. From analyzing the Lambic-style beer (starting pH 5.35), it was determined that *L. thermotolerans* BB202 was producing lactic acid during fermentation (7.33 g/L, final pH 3.60). Comparatively, *Saccharomyces* can produce acetic acid during growth in a glucose medium but has not been found to produce lactic acid.

Our research is in line with results found from wine feimentations. For example, *L. thermotolerans* TH941 in grape must was able to produce 9.57 g/L of lactic acid while *S. cerevisiae* SCM952 did not produce any. The starting pH of the grape must was 3.15 and *L. thermotolerans* and *S. cerevisiae* finished the 30 day fermentation with a pH of 2.90 and 3.06, respectively. In beer, lactic acid is typically only encountered when a contamination of lactic acid bacteria (LAB) occurs, as these bacteria are able to persist this harsh environment.

Despite initial aerobic conditions of wort, it is known that brewer's yeast sugar metabolism occurs via the Embden-Meyerhoff-Parnas glycolythic pathway; in this pathway wort sugars are metabolized to pyruvate. From there, pyruvate is decarboyxlated (via pyruvate decarboxylase) and forms $CO_2$ and acetaldehyde. Acetaldehyde is then reduced (via alcohol dehydrogenase) to form ethanol. However, pyruvate also can also be reduced to lactic acid via lactate dehydrogenase (using NADH) when oxygen is limited or absent. Thus, it is possible that *L. thermotolerans* BB202 is using lactate dehydrogenase for the formation of lactic acid. This production of lactic acid makes *L. thermotolerans* BB202 unique as brewing yeast and gives the potential to create novel single-culture sour beers that do not rely on lactic acid bacteria and mixed culture fermentations.

Aromatics were also determined for the Lambic-style beer. A noticeable difference from previous results was that the compound acetaldehyde was not detected. Acetaldehyde is the major aldehyde present in beer, as it is an intermediate of ethanol and acetate; however, acetaldehyde has a flavor threshold of 10-20 mg/L and above its threshold results in a 'grassy' flavor. High pitching rate, high fermentation temperature, and high oxygen levels result in a high acetaldehyde concentration in beer. In Phase 2 and 3 (laboratory scale), fermentations were conducted in flasks that were uncapped each day and gently swirled with the goal of achieving a homogenous sample; this practice would have increased the oxygen level of laboratory fermentations. Additionally, Phase 2 and 3 were both overpitched at $1 \times 10^7$ cfu/mL (the desired pitching rate is $1 \times 10^6$ cfu/mL). Both these practices likely attributed to the overproduction of acetaldehyde by *L. thermotolerans* BB202 in Phase 2 and 3. Meanwhile, Phase 4 was conducted in a gas-tight stainless steel fermenter, yeast was not overpitched and aromatic analysis results showed *L. thermotolerans* BB202 did not produce acetaldehyde.

While Phase 1, 2, and 3 demonstrated *L. thermotolerans* BB202 can grow in flasks at laboratory scale, Phase 4 showed that strain BB202 can grow in a stainless steel fermenter, which is the typical beer production method. This successful fermentation demonstrates that *L. thermotolerans* BB202 can be used by industry to produce beer in the brewhouse environment.

Example 7. Additional Phase 2 Data

Tables 17-20 contain the detailed HPLC data of sugars and ethanol and their corresponding statistical significance based on the calculation of standard deviations, from the fermentations performed in order to demonstrate the improved performance of *L. thermotolerans* BB202 in comparison to the type strain ATCC 56472. Tables 21-24 contain data obtained of specific gravity, pH and cell counts and their corresponding statistical significance based on the calculation of standard deviations, from the fermentations performed in order to demonstrate the improved performance of *L. thermotolerans* BB202 in comparison to the type strain ATCC 56472.

TABLE 17

Utilization of Sugars and Production of Alcohol and Sugar Alcohol Throughout Fermentation of BB202 at 18° C.

| Day of Fermentation | Maltose (g/L) | Glucose (g/L) | Fructose (g/L) | Glycerol (g/L) | Ethanol (g/L) | Alcohol by Volume (%) |
|---|---|---|---|---|---|---|
| 0 | 65.4 | 15.5 | 7.0 | 0.3 | 1.7 | 0.2% |
| 1 | 64.4 | 10.7 | 5.6 | 0.6 | 4.2 | 0.5% |
| 2 | 64.9 | 0.5 | 0.8 | 1.1 | 10.5 | 1.3% |
| 3 | 43.2 | 0.1 | 0.3 | 1.5 | 17.4 | 2.2% |
| 4 | 20.3 | 0.5 | 1.0 | 2.0 | 28.1 | 3.6% |
| 5 | 10.0 | 1.1 | 1.9 | 2.1 | 33.8 | 4.3% |
| 6 | 5.3 | 1.1 | 1.7 | 2.1 | 33.9 | 4.3% |
| 7 | 4.0 | n.d. | 2.3 | 2.0 | 32.7 | 4.2% |

TABLE 18

Standard Deviations of Sugars and Alcohols Throughout Fermentation of BB202 at 18° C.

| Day of Fermentation | Maltose (g/L) | Glucose (g/L) | Fructose (g/L) | Glycerol (g/L) | Ethanol (g/L) | Alcohol by Volume (%) |
|---|---|---|---|---|---|---|
| 0 | 4.0 | 0.7 | 0.5 | 0.0 | 0.2 | 0.0% |
| 1 | 9.3 | 2.4 | 1.3 | 0.1 | 1.1 | 0.1% |
| 2 | 10.6 | 0.2 | 0.4 | 0.1 | 1.3 | 0.2% |
| 3 | 5.5 | 0.0 | 0.1 | 0.1 | 1.5 | 0.2% |
| 4 | 4.9 | 0.4 | 0.5 | 0.1 | 1.5 | 0.2% |
| 5 | 2.6 | 0.0 | 0.1 | 0.0 | 0.5 | 0.1% |
| 6 | 1.9 | 0.0 | 1.1 | 0.3 | 4.9 | 0.6% |
| 7 | 0.0 | n.d. | 0.1 | 0.1 | 0.6 | 0.1% |

TABLE 19

Utilization of Sugars and Production of Alcohol and Sugar Alcohol Throughout Fermentation of ATCC #56472 at 18° C.

| Day of Fermentation | Maltose (g/L) | Glucose (g/L) | Fructose (g/L) | Glycerol (g/L) | Ethanol (g/L) | Alcohol by Volume (%) |
|---|---|---|---|---|---|---|
| 0 | 64.9 | 15.5 | 6.9 | 0.2 | n.d. | n.d. |
| 1 | 64.2 | 9.4 | 5.0 | 0.6 | 3.1 | 0.4% |
| 2 | 57.5 | n.d. | 0.2 | 0.9 | 8.1 | 1.0% |
| 3 | 68.3 | n.d. | 0.1 | 1.1 | 9.6 | 1.2% |
| 4 | 63.3 | n.d. | 0.1 | 1.0 | 8.7 | 1.1% |
| 5 | 62.6 | n.d. | 0.1 | 1.0 | 8.6 | 1.1% |
| 6 | 62.2 | n.d. | 0.1 | 1.0 | 8.5 | 1.1% |
| 7 | 61.4 | n.d. | 0.1 | 1.0 | 8.4 | 1.1% |

TABLE 20

Standard Deviations of Sugars and Alcohols Throughout Fermentation of ATCC #56472 at 18° C.

| Day of Fermentation | Maltose (g/L) | Glucose (g/L) | Fructose (g/L) | Glycerol (g/L) | Ethanol (g/L) | Alcohol by Volume (%) |
|---|---|---|---|---|---|---|
| 0 | 0.7 | 0.2 | 0.1 | 0.1 | n.d. | n.d. |
| 1 | 2.5 | 0.4 | 0.2 | 0.0 | 0.1 | 0.0 |
| 2 | 1.8 | n.d. | 0.1 | 0.0 | 0.2 | 0.0 |
| 3 | 4.7 | n.d. | 0.1 | 0.1 | 0.8 | 0.0 |
| 4 | 0.9 | n.d. | 0.1 | 0.0 | 0.1 | 0.0 |
| 5 | 3.7 | n.d. | 0.1 | 0.1 | 0.5 | 0.0 |
| 6 | 1.2 | n.d. | 0.1 | 0.0 | 0.2 | 0.0 |
| 7 | 1.4 | n.d. | 0.1 | 0.0 | 0.1 | 0.0 |

TABLE 21

Acid Production, Density Depletion and Cell Counts Throughout Fermentation of BB202 at 18° C.

| Day of Fermentation | pH | Density (g/cm$^3$) | Sugar (g/L) | Cell Count (cfu/mL) |
|---|---|---|---|---|
| 0 | 5.6 | 1.1 | 141.6 | $2.19 \times 10^7$ |
| 1 | 4.6 | 1.0 | 123.5 | $2.13 \times 10^7$ |
| 2 | 3.9 | 1.0 | 104.0 | $1.57 \times 10^7$ |
| 3 | 3.7 | 1.0 | 88.8 | $1.09 \times 10^7$ |
| 4 | 3.7 | 1.0 | 63.8 | $9.92 \times 10^7$ |
| 5 | 3.6 | 1.0 | 49.9 | $2.01 \times 10^7$ |
| 6 | 3.6 | 1.0 | 46.0 | $1.26 \times 10^7$ |
| 7 | 3.7 | 1.0 | 45.9 | $1.88 \times 10^7$ |

TABLE 22

Standard Deviations of Acid Production, Density Depletion and Cell Counts Throughout Fermentation of BB202 at 18° C.

| Day of Fermentation | pH | Density (g/cm$^3$) | Sugar (g/L) | Cell Count (cfu/mL) |
|---|---|---|---|---|
| 0 | 0.0 | n.d. | n.d. | 2.09 × 10$^6$ |
| 1 | 0.2 | 0.0 | 1.7 | 3.95 × 10$^6$ |
| 2 | 0.0 | 0.0 | 3.2 | 1.60 × 10$^6$ |
| 3 | 0.1 | 0.0 | 6.5 | 2.47 × 10$^6$ |
| 4 | 0.0 | 0.0 | 3.9 | 1.90 × 10$^6$ |
| 5 | 0.0 | 0.0 | 1.8 | 9.84 × 10$^6$ |
| 6 | 0.0 | 0.0 | 0.5 | 1.94 × 10$^6$ |
| 7 | 0.0 | 0.0 | 0.9 | 6.89 × 10$^6$ |

TABLE 23

Acid Production, Density Depletion and Cell Counts Throughout Fermentation of ATCC #56472 at 18° C.

| Day of Fermentation | pH | Density (g/cm$^3$) | Sugar (g/L) | Cell Count (cfu/mL) |
|---|---|---|---|---|
| 0 | 5.6 | 1.1 | 141.6 | 1.77 × 10$^7$ |
| 1 | 5.0 | 1.0 | 128.7 | 4.59 × 10$^7$ |
| 2 | 4.7 | 1.0 | 111.8 | 8.68 × 10$^7$ |
| 3 | 4.7 | 1.0 | 114.1 | 1.01 × 10$^8$ |
| 4 | 4.8 | 1.0 | 115.1 | 1.09 × 10$^8$ |
| 5 | 4.8 | 1.0 | 108.0 | 9.84 × 10$^7$ |
| 6 | 4.8 | 1.0 | 111.4 | 1.06 × 10$^8$ |
| 7 | 4.9 | 1.0 | 108.9 | 9.77 × 10$^7$ |

TABLE 24

Standard Deviations of Acid Production, Density Depletion and Cell Counts Throughout Fermentation of ATCC #56472 at 18° C.

| Day of Fermentation | pH | Density (g/cm$^3$) | Sugar (g/L) | Cell Count (cfu/mL) |
|---|---|---|---|---|
| 0 | 0.0 | n.d. | n.d. | 4.58 × 10$^6$ |
| 1 | 0.0 | 0.0 | 2.5 | 5.52 × 10$^6$ |
| 2 | 0.0 | 0.0 | 1.5 | 3.80 × 10$^6$ |
| 3 | 0.0 | 0.0 | 2.7 | 7.60 × 10$^6$ |
| 4 | 0.0 | 0.0 | 1.6 | 5.54 × 10$^6$ |
| 5 | 0.0 | 0.0 | 2.8 | 1.67 × 10$^7$ |
| 6 | 0.0 | 0.0 | 2.1 | 8.16 × 10$^6$ |
| 7 | 0.0 | 0.0 | 1.2 | 8.68 × 10$^6$ |

Example 8. Additional Phase 3 Data

Tables 25-28 contain the detailed HPLC data of sugars and ethanol and their corresponding statistical significance based on the calculation of standard deviations, from the fermentations performed in order to evaluate the performance of *L. thermotolerans* BB202 in both regular strength and high gravity wort, demonstrating the capability of this strain to brew high gravity beer. Tables 29-32 contain data obtained of specific gravity, pH and cell counts and their corresponding statistical significance based on the calculation of standard deviations, from the fermentations performed in order to evaluate the performance of *L. thermotolerans* BB202 in both regular strength and high gravity wort, demonstrating the capability of this strain to brew high gravity beer.

TABLE 25

Utilization of Sugars and Production of Alcohol and Sugar Alcohol Throughout Fermentation of BB202 at 22° C.

| Day of Fermentation | Maltose (g/L) | Glucose (g/L) | Fructose (g/L) | Glycerol (g/L) | Ethanol (g/L) | Alcohol by Volume (%) |
|---|---|---|---|---|---|---|
| 0 | 49.2 | 8.6 | 4.7 | 0.3 | 0.9 | 0.1% |
| 1 | 58.6 | 0.7 | 1.6 | 0.9 | 7.4 | 0.9% |
| 2 | 25.9 | 0.1 | 0.3 | 1.1 | 14.8 | 1.9% |
| 3 | 7.2 | 0.6 | 0.8 | 1.9 | 27.5 | 3.5% |
| 4 | 4.1 | 0.6 | 0.7 | 1.9 | 28.9 | 3.7% |

TABLE 26

Standard Deviations of Sugars and Alcohols Throughout Fermentation of BB202 at 22° C.

| Day of Fermentation | Maltose (g/L) | Glucose (g/L) | Fructose (g/L) | Glycerol (g/L) | Ethanol (g/L) | Alcohol by Volume (%) |
|---|---|---|---|---|---|---|
| 0 | 2.4 | 0.4 | 0.5 | 0.1 | 0.1 | 0.1% |
| 1 | 3.7 | 0.0 | 0.3 | 0.0 | 0.1 | 0.0% |
| 2 | 1.5 | −0.1 | 0.3 | 0.0 | 0.4 | 0.1% |
| 3 | 1.6 | 0.0 | 0.3 | 0.2 | 2.8 | 0.4% |
| 4 | 0.6 | 0.0 | 0.3 | 0.1 | 1.0 | 0.1% |

TABLE 27

Utilization of Sugars and Production of Alcohol and Sugar Alcohol Throughout Fermentation of BB202 at 22° C. in High Gravity Wort.

| Day of Fermentation | Maltose (g/L) | Glucose (g/L) | Fructose (g/L) | Glycerol (g/L) | Ethanol (g/L) | Alcohol by Volume (%) |
|---|---|---|---|---|---|---|
| 0 | 110.3 | 6.8 | 3.2 | 0.2 | 1.3 | 0.2% |
| 1 | 113.1 | 0.9 | 1.7 | 0.7 | 6.7 | 0.8% |
| 2 | 77.2 | n.d. | 0.4 | 1.2 | 16.4 | 2.1% |
| 3 | 51.1 | n.d. | 0.3 | 2.1 | 34.4 | 4.4% |
| 4 | 30.0 | n.d. | 0.3 | 2.6 | 45.7 | 5.8% |
| 5 | 18.2 | 0.1 | 0.3 | 3.0 | 51.8 | 6.6% |
| 6 | 11.5 | 0.2 | 0.4 | 2.9 | 52.0 | 6.6% |
| 7 | 8.9 | 0.6 | 0.7 | 3.1 | 56.0 | 7.1% |

TABLE 28

Standard Deviations of Sugars and Alcohols Throughout Fermentation of BB202 at 22° C. in High Gravity Wort.

| Day of Fermentation | Maltose (g/L) | Glucose (g/L) | Fructose (g/L) | Glycerol (g/L) | Ethanol (g/L) | Alcohol by Volume (%) |
|---|---|---|---|---|---|---|
| 0 | 8.5 | 0.3 | 0.4 | 0.0 | 0.3 | 0.0% |
| 1 | 7.5 | 0.0 | 0.3 | 0.0 | 0.1 | 0.0% |
| 2 | 9.3 | n.d. | 0.3 | 0.1 | 1.5 | 0.2% |
| 3 | 6.2 | n.d. | 0.3 | 0.1 | 1.7 | 0.2% |
| 4 | 3.0 | n.d. | 0.3 | 0.1 | 1.0 | 0.1% |
| 5 | 1.5 | 0.0 | 0.3 | 0.2 | 1.3 | 0.2% |
| 6 | 1.0 | 0.1 | 0.4 | 0.1 | 1.4 | 0.2% |
| 7 | 1.1 | 0.1 | 0.3 | 0.0 | 1.1 | 0.1% |

TABLE 29

Acid Production, Density Depletion and Cell Counts Throughout Fermentation of BB202 at 22° C.

| Day of Fermentation | pH | Density (g/cm³) | Sugar (g/L) | Cell Count (cfu/mL) |
|---|---|---|---|---|
| 0 | 5.28 | 1.043 | 116.7 | $1.54 \times 10^7$ |
| 1 | 3.91 | 1.039 | 106.0 | $1.65 \times 10^7$ |
| 2 | 3.62 | 1.027 | 75.1 | $1.46 \times 10^7$ |
| 3 | 3.50 | 1.017 | 48.1 | $1.35 \times 10^7$ |
| 4 | 3.54 | 1.015 | 43.9 | $1.26 \times 10^7$ |

TABLE 30

Standard Deviations of Acid Production, Density Depletion and Cell Counts Throughout Fermentation of BB202 at 22° C.

| Day of Fermentation | pH | Density (g/cm³) | Sugar (g/L) | Cell Count (cfu/mL) |
|---|---|---|---|---|
| 0 | 0.02 | 0.001 | 2.1 | $5.55 \times 10^6$ |
| 1 | 0.01 | 0.000 | 0.8 | $1.78 \times 10^6$ |
| 2 | 0.02 | 0.001 | 2.7 | $3.62 \times 10^6$ |
| 3 | 0.00 | 0.002 | 3.9 | $2.16 \times 10^6$ |
| 4 | 0.01 | 0.000 | 0.7 | $4.73 \times 10^6$ |

TABLE 31

Acid Production, Density Depletion and Cell Counts Throughout Fermentation of BB202 at 22° C. in High Gravity Wort.

| Day of Fermentation | pH | Density (g/cm³) | Sugar (g/L) | Cell Count (cfu/mL) |
|---|---|---|---|---|
| 0 | 5.26 | 1.064 | 172.8 | $9.67 \times 10^6$ |
| 1 | 3.96 | 1.060 | 160.8 | $1.91 \times 10^7$ |
| 2 | 3.63 | 1.048 | 130.6 | $1.20 \times 10^7$ |
| 3 | 3.47 | 1.032 | 87.8 | $1.23 \times 10^7$ |
| 4 | 3.46 | 1.023 | 64.3 | $1.50 \times 10^7$ |
| 5 | 3.47 | 1.018 | 51.2 | $4.50 \times 10^7$ |
| 6 | 3.52 | 1.015 | 42.8 | $1.84 \times 10^7$ |
| 7 | 3.54 | 1.013 | 39.5 | $2.31\text{E}+0^7$ |

TABLE 32

Standard Deviations of Acid Production, Density Depletion and Cell Counts Throughout Fermentation of BB202 at 22° C. in High Gravity Wort.

| Day of Fermentation | pH | Density (g/cm³) | Sugar (g/L) | Cell Count (cfu/mL) |
|---|---|---|---|---|
| 0 | 0.00 | 0.001 | 3.9 | $1.41 \times 10^6$ |
| 1 | 0.01 | 0.002 | 4.1 | $4.28 \times 10^6$ |
| 2 | 0.04 | 0.002 | 4.3 | $1.68 \times 10^6$ |
| 3 | 0.01 | 0.001 | 3.1 | $2.49 \times 10^6$ |
| 4 | 0.01 | 0.001 | 2.3 | $7.97 \times 10^6$ |
| 5 | 0.02 | 0.000 | 1.2 | $5.77 \times 10^6$ |
| 6 | 0.00 | 0.000 | 1.1 | $4.47 \times 10^6$ |
| 7 | 0.01 | 0.001 | 1.7 | $4.09 \times 10^6$ |

Example 9. Additional Phase 4 Data

Tables 33-34 contain the detailed HPLC data of sugars, lactic acid, glycerol and ethanol, and pH (by off-line probe) obtained by the analysis of samples from the pilot-scale Lambic fermentation conducted with strain *L. thermotolerans* BB202, demonstrating the ability of this strain to produce a sour Lambic-style beer in as short as 25 days.

TABLE 33

HPLC analysis of Lambic sugar utilization.

| Day | Maltotriose (g/L) | Maltose (g/L) | Glucose (g/L) | Fructose (g/L) | Total Sugars (g/L) |
|---|---|---|---|---|---|
| 0 | 29.0 | 67.0 | 18.7 | 6.8 | 121.5 |
| 1 | 25.5 | 62.7 | 15.0 | 6.6 | 109.8 |
| 2 | 27.5 | 66.5 | 11.6 | 6.1 | 111.7 |
| 3 | 27.5 | 66.2 | 5.1 | 4.3 | 103.1 |
| 4 | 24.5 | 59.4 | 0.6 | 1.7 | 86.2 |
| 5 | 27.4 | 65.7 | n.d. | 1.4 | 94.4 |
| 6 | 25.2 | 60.6 | n.d. | 0.7 | 86.4 |
| 7 | 27.9 | 65.9 | n.d. | 0.7 | 94.5 |
| 8 | 23.0 | 55.1 | n.d. | 0.5 | 78.6 |
| 9 | 25.0 | 59.5 | n.d. | 0.6 | 85.0 |
| 12 | 23.9 | 56.5 | n.d. | 0.5 | 81.0 |
| 13 | 22.1 | 50.3 | 0.7 | 0.4 | 73.6 |
| 14 | 13.4 | 29.8 | 1.1 | n.d. | 44.4 |
| 15 | 13.4 | 25.9 | 1.1 | n.d. | 40.4 |
| 16 | 13.4 | 22.9 | 1.3 | n.d. | 37.6 |
| 17 | 9.6 | 17.5 | 1.7 | n.d. | 28.7 |
| 18 | 8.1 | 15.2 | 1.5 | n.d. | 24.8 |
| 19 | 6.9 | 12.7 | 1.4 | n.d. | 20.9 |
| 20 | 5.1 | 9.7 | 1.0 | n.d. | 15.8 |
| 25 | 4.8 | 3.5 | 0.8 | n.d. | 9.0 |
| 33 | 4.7 | 3.1 | 0.5 | n.d. | 8.3 |
| 41 | 4.6 | 3.0 | 0.6 | n.d. | 8.2 |
| Δ Utilized | 24.4 | 64.0 | 18.1 | 6.8 | 113.3 |
| % Utilized | 84% | 96% | 97% | 100% | 93% |

TABLE 34

Lactic acid, pH, glycerol and ethanol analysis of Lambic fermentation.

| Day | pH | Lactic Acid (g/L) | Glycerol (g/L) | Ethanol (g/L) | ABV (%) |
|---|---|---|---|---|---|
| 0 | 5.4 | n.d. | n.d. | n.d. | n.d. |
| 1 | 5.3 | 1.0 | n.d. | n.d. | n.d. |
| 2 | 4.5 | 2.4 | n.d. | 1.6 | 0.2% |
| 3 | 4.0 | 3.8 | 0.6 | 5.6 | 0.7% |
| 4 | 3.6 | 6.1 | 1.1 | 7.5 | 1.0% |
| 5 | 3.6 | 6.9 | 1.3 | 9.0 | 1.1% |
| 6 | 3.6 | 6.3 | 1.2 | 8.6 | 1.1% |
| 7 | 3.6 | 7.0 | 1.4 | 9.5 | 1.2% |
| 8 | 3.6 | 5.7 | 1.1 | 7.8 | 1.0% |
| 9 | 3.6 | 6.4 | 1.2 | 8.8 | 1.1% |
| 12 | 3.6 | 6.9 | 1.3 | 11.6 | 1.5% |
| 13 | 3.6 | 7.4 | 1.6 | 17.2 | 2.2% |
| 14 | 3.6 | 5.3 | 1.1 | 18.0 | 2.3% |
| 15 | 3.6 | 6.1 | 1.4 | 24.7 | 3.1% |
| 16 | 3.6 | 7.6 | 1.9 | 36.6 | 4.6% |
| 17 | 3.6 | 7.6 | 2.1 | 42.5 | 5.4% |
| 18 | 3.6 | 7.4 | 2.1 | 43.5 | 5.5% |
| 19 | 3.6 | 7.5 | 2.2 | 47.1 | 6.0% |
| 20 | 3.6 | 6.9 | 2.0 | 45.0 | 5.7% |
| 25 | 3.6 | 7.4 | 2.4 | 54.0 | 6.8% |
| 33 | 3.6 | 7.5 | 2.4 | 55.3 | 7.0% |
| 41 | 3.6 | 7.3 | 2.4 | 53.8 | 6.8% |

Example 10. Alcoholic Cider

Pasteurized, unfiltered, organic apple juice with no preservatives or added sugar (for example, Martinelli's apple juice (Watsonville Calif.)) was fermented with *L. thermotolerans* strain BB202 inoculated at 1×10E7 cells per mL. The fermentation conditions were 3×250 mL in 500 mL Erlenmeyer flasks, no agitation, 22 degrees C. Ethanol, glucose, fructose and glycerol were analyzed by HPLC, pH by portable meter. Results of the analysis are shown in Table 35.

TABLE 35

Analysis of fermentation of apple juice by BB202

| Day | Fructose (g/L) | Glucose (g/L) | Glycerol (g/L) | Ethanol (g/L) | Ethanol (v/v) | pH |
|---|---|---|---|---|---|---|
| 0 | 60.4 | 30.3 | ND | ND | ND | 3.73 |
| 4 | 19 | 2.8 | 3.5 | 44.7 | 5.70% | 3.3 |
| 9 | 1 | 0.5 | 3.7 | 50.6 | 6.40% | 3.36 |

Fermentation of *L. thermotolerans* strain BB202 with apple juice produced a palatable alcoholic cider, with a light refreshing apple aroma and no discernible off-flavors. Approximately 76% of the fermentable sugar was used in the first 4 days, resulting in 5.7% ethanol by volume. After 9 days, over 98% of the sugar was utilized by the yeast, reaching a final ethanol concentration of 6.4% by volume. In addition, the pH of the apple juice was lowered from 3.73 to 3.36.

The foregoing is illustrative of the present invention, and is not to be construed as limiting thereof. The invention is defined by the following claims, with equivalents of the claims to be included therein.

That which is claimed is:

1. A method of producing a sour fermented beverage comprising fermenting brewer's wort prepared from malted grain with a yeast species, wherein the brewer's wort comprises maltose and/or maltotriose, and the yeast species is *Lachancea thermotolerans* strain YB16 deposited as NRRL Y-67252 and/or *Lachancea thermotolerans* strain BB202 deposited as NRRL Y-67253, each of which have the ability to metabolize maltose and/or maltotriose, produce lactic acid, and produce at least 0.5% (about 3.9 g/L) ethanol, thereby producing a sour fermented beverage having a pH of 3.8 or lower.

2. The method of claim 1, wherein the grain is barley, rye, wheat, corn, sorghum, rice, or any combination thereof.

3. The method of claim 1, wherein the grain is barley.

4. The method of claim 1, wherein the amount of lactic acid produced is about 4 g/L to about 8 g/L.

5. The method of claim 1, wherein the amount of ethanol is at least about 0.5% (about 3.9/L) to about 6.5% (about 50 g/L).

6. The method of claim 1, further comprising fermenting in the presence of *Saccharomyces cerevisiae* and/or *Saccharomyces pastorianus*.

7. The method of claim 1, wherein the sour fermented beverage is ale, or lager beer.

* * * * *

UNITED STATES PATENT AND TRADEMARK OFFICE
CERTIFICATE OF CORRECTION

PATENT NO. : 11,008,539 B2
APPLICATION NO. : 15/573652
DATED : May 18, 2021
INVENTOR(S) : Sheppard et al.

It is certified that error appears in the above-identified patent and that said Letters Patent is hereby corrected as shown below:

In the Specification

Column 3, Line 44: Please correct "+1" to read -- ±1 --

Column 3, Line 51: Please correct "+1" to read -- ±1 --

Column 29, Line 32: Please correct "arid" to read -- and --

Column 34, Line 9: Please correct "A 1.91" to read -- Δ 1.91 --

Column 34, Line 10: Please correct "A 0.69" to read -- Δ 0.69 --

Signed and Sealed this
Twenty-first Day of September, 2021

Drew Hirshfeld
*Performing the Functions and Duties of the*
*Under Secretary of Commerce for Intellectual Property and*
*Director of the United States Patent and Trademark Office*